United States Patent [19]

Takaya et al.

[11] 4,349,552
[45] Sep. 14, 1982

[54] 5-FLUOROURACIL DERIVATIVES, AND THEIR PHARMACEUTICAL COMPOSITIONS

[75] Inventors: Takao Takaya, Kawanishi; Zenzaburo Tozuka, Toyonaka, both of Japan

[73] Assignee: Fujisawa Pharmaceutical Company, Ltd., Osaka, Japan

[21] Appl. No.: 111,643

[22] Filed: Jan. 14, 1980

Related U.S. Application Data

[63] Continuation-in-part of Ser. No. 89,399, Oct. 30, 1979, abandoned.

[30] Foreign Application Priority Data

Oct. 30, 1978 [GB] United Kingdom ............... 42426/78
Jan. 22, 1979 [GB] United Kingdom ................ 7902195
Mar. 19, 1979 [GB] United Kingdom ................ 7909522
Jun. 4, 1979 [GB] United Kingdom ................ 7919439
Oct. 29, 1979 [CA] Canada ................................. 338650
Oct. 30, 1979 [JP] Japan .............................. 54-140983

[51] Int. Cl.$^3$ ........................................... C07D 239/30
[52] U.S. Cl. .................................... 424/251; 544/313; 544/311
[58] Field of Search ................................ 544/313, 311

[56] References Cited

U.S. PATENT DOCUMENTS 3,971,784 7/1976 Tada .................................... 544/313
4,032,524 6/1977 Ozaki et al. ......................... 424/251
4,071,519 1/1978 Ozaki .................................. 544/311
4,088,646 5/1978 Ishida et al. ........................ 424/251

FOREIGN PATENT DOCUMENTS 2455423 6/1975 Fed. Rep. of Germany .
52-1157 8/1978 Japan .

OTHER PUBLICATIONS

CA vol. 88, No. 3, p. 644 22966p (1972).

Primary Examiner—Nicholas S. Rizzo
Attorney, Agent, or Firm—Oblon, Fisher, Spivak, McClelland & Maier

[57] ABSTRACT

A compound of the formula:

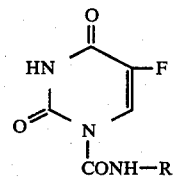

wherein R is a bridged alicyclic group selected from the group consisting of norbornyl, norbornenyl, bicyclo[2,2,2]-heptyl and adamantyl optionally substituted by at least one substituent selected from the group consisting of lower alkyl, carboxy, lower alkoxycarbonyl, alkylidenedioxy, N,N-di(lower)alkylcarbamoyl, amino, loweralkoxycarbonylamino and halogen. The present compound is useful in the therapeutic treatment of cancer in human beings and animals.

39 Claims, No Drawings

5-FLUOROURACIL DERIVATIVES, AND THEIR PHARMACEUTICAL COMPOSITIONS

CROSS REFERENCE TO RELATED APPLICATION

This application is a continuation-in-part of application Ser. No. 089,399 filed Oct. 30, 1979, now abandoned.

This invention relates to new 5-fluorouracil derivatives and their pharmaceutically acceptable salts.

More particularly, it relates to new 5-fluorouracil derivatives and their pharmaceutically acceptable salts which have antitumor activity, to processes for the preparation thereof, to pharmaceutical compositions comprising the same and to a method of using the same for therapeutic treatment of cancer in human being and animals.

Accordingly, it is one object of this invention to provide new 5-fluorouracil derivatives and their pharmaceutically acceptable salts, which are strongly active as antitumor agent.

Another object of this invention is to provide processes for the preparation of new 5-fluorouracil derivatives and their pharmaceutically acceptable salts.

A further object of this invention is to provide pharmaceutical compositions comprising said new 5-fluorouracil derivatives or their pharmaceutically acceptable salts.

Still further object of this invention is to provide a method for therapeutic treatment of cancer in human being and animals.

The object compounds, 5-fluorouracil derivatives of this invention are novel and can be represented by the following formula:

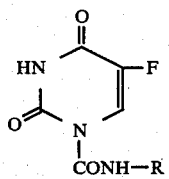

(I)

wherein R is
bridged alicyclic group which may have suitable substituent(s);
substituted lower alkyl group, the substituent being selected from bridged alicyclic group which may have suitable substituent(s), amino, protected amino, lower alkoxy, acyl, lower alkylthio, cyano(lower)alkylthio, arylthio, heterocyclic group which may have suitable substituent(s), carboxy and esterified carboxy, provided that when the substituent is carboxy or esterified carboxy, then carbon numbers of the lower alkyl are 3 to 6;
unsubstituted or substituted lower alkenyl group, the substituent being selected from bridged alicyclic group which may have suitable substituent(s), aryl which may have suitable substituent(s) and heterocyclic group which may have suitable substituent(s);
halophenyl; or
heterocyclic group which may have suitable substituent(s).

In the above and subsequent description of this specification, suitable examples and illustrations for the various definitions for the symbol "R", which this invention intends to include within the scope thereof, are explained in details as follows.

The term "lower" is intended to mean a group having 1 to 6 carbon atom(s), unless otherwise provided.

(1) Bridged alicyclic group which may have suitable substituent(s):

The "bridged alicyclic group" in "bridged alicyclic group which may have suitable substituent(s)" may include a group derived from a saturated or unsaturated, bridged, bicyclic or tricyclic hydrocarbon, particularly including bridged bicyclicalkyl, bridged bicyclicalkenyl, bridged tricyclicalkyl and bridged tricyclicalkenyl in which the carbon numbers are preferably 6 to 12, and more preferably 7 to 10.

And, as preferred examples of said bridged alicyclic group, there may more particularly be exemplified bicyclo[3.1.0]hexyl, bicyclo[3.1.0]-2-hexenyl, bicyclo[4.1.0]heptyl (alternatively, norcaranyl), bicyclo[4.1.0]-2-heptenyl, bicyclo[4.1.0]-3-heptenyl, bicyclo[3.1.1]heptyl, bicyclo[3.1.1]-2-heptenyl, bicyclo[2.2.1]heptyl (alternatively, norbornyl), bicyclo[2.2.1]-2-heptenyl (alternatively, norbornenyl), bicyclo[2.2.1]-2,5-heptdienyl, bicyclo[2.2.2]octyl, bicyclo[2.2.2]-2-octenyl, bicyclo[2.2.2]-2,5-octdienyl, tricyclo[3.3.1.1$^{3,7}$]decyl (alternatively, admantyl) and the like.

As the "suitable substituent(s)" in "bridged alicyclic group which may have suitable substituent(s)", there may be exemplified lower alkyl (e.g. methyl, ethyl, propyl, isopropyl, butyl, isobutyl, tert-butyl, etc.), in which preferred carbon number is 1 to 4; carboxy; hydroxy; esterified carboxy such as lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, etc.); alkylidenedioxy (e.g. methylenedioxy, ethylenedioxy, propylidenedioxy, etc.); N,N-di(lower)alkylcarbamoyl (e.g. N,N-dimethylcarbamoyl, N,N-diethylcarbamoyl, N,N-dipropylcarbamoyl, N,N-diisopropylcarbamoyl, etc.); amino; protected amino; halogen (fluorine, chlorine, bromine, iodine) and the like. And, as "amino protective group" in the "protected amino", there may be exemplified the same one as described below as that of "protected amino" of the substituted lower alkyl group for R.

Among the "bridged alicyclic group which may have suitable substituent(s)" as explained above, the particularly preferred examples thereof exemplified below:
for "bridged alicyclic group", norbornyl
  (e.g. 2-norbornyl, etc.),
  norbornenyl
  (e.g. 5-norbornen-2-yl, etc.),
  bicyclo[2.2.2]octyl
  (e.g. bicyclo[2.2.2]oct-2-yl, etc.),
  adamantyl
  (e.g. 1-adamantyl, etc.),
  bicyclo[3.1.0]hexyl
  (e.g. bicyclo[3.1.0]hex-2-yl, etc.),
  bicyclo[4.1.0]heptyl
  (e.g. bicyclo[4.1.0]hept-2-yl, etc.),
  and the like,
and
  for "bridged alicyclic group which has suitable substituent(s),"
  carboxynorbornyl (e.g. 3-carboxy-2-norbornyl, etc.), (lower)alkoxycarbonylnorbornyl (e.g. 3-methoxycarbonylnorborn-2-yl, 3-ethoxycarbonylnorborn-2-yl, 3-isopropoxycarbonylnorborn-2-yl, etc.),
[N,N-di(lower)alkylcarbamoyl]norbornyl (e.g. 3-(N,N-diisopropylcarbamoyl)-2-norbornyl, etc.,)
aminonorbornyl (e.g. 3-amino-2-norbornyl, etc.),
(lower)alkoxycarbonylalkylidenedioxynorbornyl (e.g. 3-ethoxycarbonyl-5,6-isopropylidenedioxy-2-norbornyl, etc.),
carboxynorbornenyl (e.g. 3-carboxy-5-norbornen-2-yl, etc.),
(lower)alkoxycarbonylnorbornenyl (e.g. 3-methoxycarbonyl-5-norbornen-2-yl, 3-ethoxycarbonyl-5-norbornen-2-yl, 3-isopropoxycarbonyl-5-norbornen-2-yl, 3-tert-butoxycarbonyl-5-norbornen-2-yl, etc.), (lower)alkoxycarbonylbicyclo[2.2.2]octyl (e.g. 3-ethoxycarbonylbicyclo[2.2.2]oct-2-yl,
haloadamantyl (e.g. 3-bromoadamantyl, etc.)
bicyclo[3.1.1]heptyl substituted by lower alkyl (e.g. pinanyl, etc.), and the like.

(2) Substituted lower alkyl group:
"Lower alkyl" moiety in "substituted lower alkyl" group may include straight and branched lower alkyl such as methyl, ethyl, propyl, isopropyl, butyl, isobutyl, pentyl, hexyl or the like, and preferably the straight ones.

"The substituent" as defined in R for the substituent of the "substituted lower alkyl" are more particularly explained in the following:

"Bridged alicyclic group which may have suitable substituent(s)" may be the same as those explained in the above paragraph (1) for the "bridged alicyclic group which may have suitable substituent(s)", and particularly are to be referred to the detailed explanation made there for each of "bridged alicyclic group" and "suitable substituent(s)" in "bridged alicyclic group which may have substituent(s)", "Amino protective group" in the "protected amino" may include a conventional N-protective group such as acyl, substituted or unsubstituted ar(lower)alkyl (e.g. benzyl, chlorobenzyl, methoxybenzyl, phenethyl, benzhydryl, trityl, etc.) or the like. The preferred acyl for the protective group may be substituted or unsubstituted alkanoyl such as lower alkanoyl (e.g. formyl, acetyl, etc.), halo(lower)alkanoyl (e.g. chloroacetyl, trifluoroacetyl, dichloroacetyl, etc.) or the like; substituted or unsubstituted lower alkoxycarbonyl such as lower alkoxycarbonyl (e.g. methoxycarbonyl, t-butoxycarbonyl, etc.), halo(lower)alkoxycarbonyl (e.g. dichloroethoxycarbonyl, trichloroethoxycarbonyl, etc.) or the like; substituted or unsubstituted ar(lower)alkoxycarbonyl (e.g. benzyloxycarbonyl, benzhydryloxycarbonyl, chlorobenzyloxycarbonyl, nitrobenzyloxycarbonyl, methoxybenzyloxycarbonyl, etc.) and the like.

"Lower alkoxy" may include straight and branched lower alkoxy such as methoxy, ethoxy, propoxy, isopropoxy, butoxy, isobutoxy, t-butoxy, pentyloxy, hexyloxy or the like, and preferably C1 to C4 lower alkoxy group.

"Acyl" may include N-substituted carbamoyl, aliphatic acyl, acyl comprising aromatic ring (heteinafter referred to aromatic acyl) and acyl comprising heterocyclic ring (hereinafter referred to heterocyclic acyl), preferred examples of which are as follows.

Preferred N-substituted carbamoyl may include N-monosubstituted carbamoyl and N,N-disubstituted carbamoyl such as N-mono or N,N-di(lower)alkylcarbamoyl (e.g. N-methylcarbamoyl, N-ethylcarbamoyl, N-propylcarbamoyl, N-isopropylcarbamoyl, N-butylcarbamoyl, N-isobutylcarbamoyl, N-pentylcarbamoyl, etc., or N,N-dimethylcarbamoyl, N,N-diethylcarbamoyl, N,N-dipropylcarbamoyl, N,N-diisopropylcarbamoyl, N,N-dibutylcarbamoyl, N,N-dipentylcarbamoyl, etc.), N-mono or N,N-di(lower)alkenylcarbamoyl (e.g. N-allylcarbamoyl, N-(2-butenyl)carbamoyl, N-methallylcarbamoyl etc., or N,N-diallylcarbamoyl, N,N-(2-butenyl)carbamoyl, N,N-dimethallylcarbamoyl etc.) or the like;

preferred aliphatic acyl may be lower alkanoyl (e.g. formyl, acetyl, propionyl, butyryl, isobutyryl, pentanoyl, hexanoyl, etc.) and the like;

preferred aromatic acyl may include aroyl(e.g. benzoyl, toluoyl, naphthoyl, etc.), aryloxycarbonyl (e.g. phenoxycarbonyl, naphthyloxycarbonyl, etc.), aryloxy(lower)alkanoyl (e.g. phenoxyacetyl, phenoxypropionyl, etc.) and the like;

heterocyclic acyl may include 3- to 7-membered heterocyclic carbonyl, in which heterocyclic ring contains 1 to 3 hetero atom(s) selected from nitrogen, oxygen and sulfur atom(s) (e.g. nicotinoyl, isonicotinoyl, thenoyl, furancarbonyl, prolyl, morpholinocarbamoyl, morpholinylcarbonyl, 4-methyl-1-piperazinocarbonyl, etc.), 3- to 7-membered heterocyclic lower alkanoyl, in which heterocyclic ring contains 1 to 4 hetero atom(s) selected from nitrogen, oxygen and sulfur atom(s) (e.g. thienylacetyl, morpholinoacetyl, tetrazylacetyl, etc.), and the like.

Lower alkyl moiety in the "lower alkylthio" and "cyano(lower)alkylthio" may include the same ones as those illustrated hereinabove for lower alkyl in the "substituted lower alkyl group". Particularly, preferred "loweralkylthio" may be methylthio, ethylthio, propylthio, isopropylthio, butylthio, isobutylthio, t-butylthio, pentylthio, hexylthio and the like, and preferred "cyano(lower)alkylthio" may be the corresponding cyano(lower)alkylthio, for example, cyanomethylthio, cyanoethylthio and the like.

"Arylthio" for the substituent of the substituted lower alkyl group may include phenylthio and the like.

"Heterocyclic group" in the "heterocyclic group which may have suitable substituent(s)" may include a 3- to 7-membered (preferably 5- to 6-membered)heterocyclic group containing 1 to 4 heteroatom(s) selected from nitrogen, oxygen and sulfur atom(s) such as unsaturated heteromonocyclic group (e.g. pyrrolyl, furyl, thienyl, pyrrolinyl, imidazolyl, pyrazolyl, pyridyl, tetrazolyl, etc.); saturated heteromonocyclic group (e.g. pyrrolidinyl, imidazolidinyl, piperidinyl, tetrahydrothienyl, dithiolanyl, etc.) or the like.

And, the substituent(s) for said heterocyclic group may include lower alkyl (e.g. methyl, ethyl, etc.), oxo and the like, and, as a preferred example of such heterocyclic group having the substituent, there is exemplified dioxopyrrolidinyl (e.g. 2,5-dioxopyrrolidin-1-yl, etc.) and the like.

"Esterified carboxy" may include lower alkoxycarbonyl (e.g. methoxycarbonyl, ethoxycarbonyl, propoxycarbonyl, isopropoxycarbonyl, butoxycarbonyl, tert-butoxycarbonyl, pentyloxycarbonyl, etc.) and the like.

(3) Unsubstituted or substituted lower alkenyl group:

"Lower alkenyl" and alkenyl moiety in the "unsubstituted or substituted alkenyl" group may include unsaturated(C2 to C6)aliphatic hydrocarbon residue such as straight and branched(C2 to C6)alkenyl (e.g. vinyl, allyl, isopropenyl, butenyl, isobutenyl, pentenyl, hexenyl, etc.), and straight and branched C4 to C6 alkadienyl (e.g. butadienyl, 1,4-pentadienyl, 1-methylbutadienyl, hexadienyl, etc.). "The substituent" as defined in R for the substituent of the "substituted lower alkenyl" are more particularly explained in the following:

"Bridged alicyclic group which may have suitable substituent(s)" may be the same as those explained in the paragraph (1) for the "bridged alicyclic group which may have suitable substituent(s)" as explained in the above paragraph (1), and particularly are to be referred to the detailed explanation made there for each of "bridged alicyclic group" and "suitable substituent(s)" in "bridged alicyclic group which may have substituent(s)".

"Aryl" in the "aryl which may have suitable substituent(s)" may be phenyl, tolyl, naphthyl, and the "suitable substituent(s)" for said aryl may be halogen (e.g. chloro, bromo, fluoro, etc.), lower alkoxy (e.g. methoxy, ethoxy, etc.) and the like.

Preferred example of such substituted aryl may be a mono- or di halophenyl (e.g. chlorophenyl, dichlorophenyl, etc.), mono-, di- or tri- lower alkoxy (e.g. methoxyphenyl, dimethoxyphenyl, trimethoxyphenyl, etc.) and the like.

"Heterocyclic group which may have suitable substituent(s)" may be the same as those explained in the above paragraph (2) and particularly are to be referred to the explanation made there for "heterocyclic group" and the substituent thereof.

(4) "Halophenyl group" may include chlorophenyl (e.g. 4-chlorophenyl, etc.) and the equivalent thereof such as bromophenyl, iodophenyl or fluorophenyl.

(5) "Heterocyclic group which may have suitable substituent(s)" may be the same as those explained in the above paragraph (2) and particularly are to be referred to the explanation made there for "heterocyclic group" and the substituent thereof.

In connection with the above definition for R, it is to be noted that the term "substituted lower alkyl, the substituent being selected from bridged alicyclic group which may have suitable substituent(s), amino, protected amino, lower alkoxy, acyl, lower alkylthio, cyano(lower)alkylthio, arylthio, heterocyclic group which may have suitable substituent(s), carboxy and esterified carboxy" can alternatively be referred to as the term "bridged alicyclic(lower)alkyl in which the bridged alicyclic moiety may have suitable substituent(s), amino(lower)alkyl, protected amino(lower)alkyl, lower alkoxy(lower)alkyl, acyl(lower)alkyl, lower alkylthio(lower)alkyl, cyano(lower)alkylthio(lower)alkyl, arylthio(lower)alkyl, heterocyclic(lower)alkyl in which the heterocyclic(lower)alkyl moiety may have suitable substituent(s), carboxy(lower)alkyl or esterified carboxy(lower)alkyl", correspondingly, and that the term "substituted lower alkenyl, the substituent being selected from bridged alicyclic group which may have suitable substituent(s), aryl which may have suitable substituent(s) or heterocyclic group which may have suitable substituent(s)" can alternatively be referred to as the term "bridged alicyclic lower alkenyl in which the bridged alicyclic moiety may have suitable substituent(s), ar(lower)alkenyl in which the aryl moiety may have suitable substituent(s) or heterocyclic lower alkenyl in which the heterocyclic moiety may have suitable substituent(s)", correspondingly.

And, as to the alternative expression of the definition for R, it is to be noted that the illustration and preferred examples as explained hereinabove for the substituents for the "substituted lower alkyl" and "substituted lower alkenyl" are applied correspondingly to each of the moieties of the group in said alternative expression of the definition.

"Pharmaceutically acceptable salts" of the object compounds (I) may be conventional non-toxic salts and may include an organic acid addition salt (e.g. maleate, tartrate, methanesulfonate, benzenesulfonate, toluenesulfonate etc.), an inorganic acid addition salt (e.g. hydrochloride, hydrobromide, sulfate, phosphate, etc.), a salt with an amino acid (e.g. arginine, aspartic acid, lysine, glutamic acid, etc.) and the like an inorganic base salt (e.g. alkali metal salt such as sodium salt, potassium salt, etc., alkaline earth metal salt such as calcium salt, magnesium salt, etc.), ammonium salt, organic base salt, for example, amine salt (e.g. trimethylamine salt, triethylamine salt, ethanolamine salt, diethanolamine salt, triethanolamine salt, pyridine salt, dicyclohexylamine salt, etc.) and the like. As to the stereochemistry of the object compounds (I) and the related compounds (e.g. starting compounds, intermediate compounds, etc.) of this invention, it is to be understood that there may be one or more stereoisomeric pair(s) of those compounds such as optical and/or geometrical isomers due to the asymmetric carbon atom(s) (e.g. of bridged alicyclic group) and/or double bond(s) (e.g. of alkenyl group) in their molecule, and such stereo isomers are also included within the scope of this invention.

The processes for preparing the object compounds (I) of this invention will be explained in detail in the following.

The process for preparing the object compounds (I) of this invention will be explained in detail in the following.

Process 1

The 5-fluorouracil derivatives (I) of this invention can be prepared by the following process.

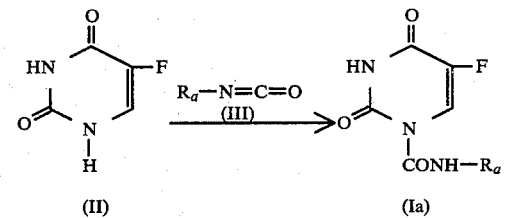

wherein $R_a$ is
bridged alicyclic group which may have suitable substituent(s);
substituted lower alkyl group, the substituent being selected from bridged alicyclic group which may have suitable substituent(s), protected amino, lower alkoxy, acyl, lower alkylthio, cyano(lower-)alkylthio, arylthio, heterocyclic group which may have suitable substituent(s) and esterified carboxy, provided that when the substituent is esterified carboxy, then carbo numbers of the lower alkyl are 3 to 6;

unsubstituted or substituted lower alkenyl group, the substituent being selected from bridged alicyclic group which may have suitable substituent(s), aryl which may have suitable substituent(s) and heterocyclic group which may have suitable substituent(s);

halophenyl; or heterocyclic group which may have suitable substituent(s).

The object compounds(Ia) or salts thereof can be prepared by reacting 5-fluorouracil (II) with isocyanate compounds of the formula (III). The reaction is usually conducted in a conventional solvent such as benzene, dimethylsulfoxide, N,N-dimethylformamide, N,N-dimethylacetamide, tetrahydrofuran, acetonitrile, methylene chloride, ethylacetate, diethyl ether, methylethylketone, pyridine, or any other solvent which does not adversely influence to the reaction under an anhydrous condition.

The reaction temperature is not critical and the reaction is preferably conducted at ambient temperature or under heating.

The object compounds (Ia) can be isolated from the reaction mixture and purified by a conventional manner.

As to this proces, it is to be noted that the reaction of this process may conveniently be conducted by adding the 5-fluorouracil (II) directly into the reaction mixture containing the isocyanate (III) which can be prepared as illustrated in the following.

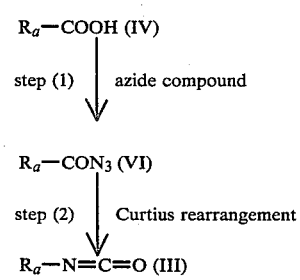

wherein $R_a$ is as defined above.

The step (1) of this process, i.e. preparation of the acid azide (VI) is conventionally conducted by reacting the carboxylic acid (IV) or its reactive derivative at the carboxy group with an azide compound.

Suitable reactive derivative at the carboxylic acid (IV) may include, for example, an acid halide (e.g. acid chloride, acid bromide, etc.), an acid anhydride which includes a mixed acid anhydride such as a mixed acid anhydride with alkylcarbonic acid which can be prepared by reacting the carboxylic acid (IV) with an alkyl halocarbonate (e.g. ethyl chlorocarbonate, etc.) and the like.

Suitable azide compound may include hydrazoic acid or its salts such as alkalimetal salt (e.g. sodium azide, potassium azide, etc.); phosphoryl azide of the formula (V) which will be illustrated herein-after and the like.

The reaction of the free form of carboxylic acid (IV) with an alkalimetal salt of hydrazoic acid can be accelerated by a catalytic amount of strong acid such as sulfuric acid, etc., and this first step can be preferably and conveniently conducted by reacting the acid halide form or acid anhydride form (preferably mixed acid anhydride form) of the carboxylic acid (IV) with an alkalimetal salt of hydrazoic acid. The reaction of the carboxylic acid (IV) with a phosphoryl azide of the formula (V) will be explained hereinafter.

The reaction of this step is usually conducted under a hydrous condition, i.e. in water or aqueous solution of water missible solvent such as alcohol (e.g. methanol, ethanol, etc.), dimethylformamide, ethylacetate or the like. The reaction is usually conducted at the range of cooling to an ambient temperature.

The second step of this process (i.e. step 2) i.e. preparation of the isocyanate (III), is conducted by subjecting the acid azide (VI) to so-called Curtius rearrangement. Curtius rearrangement of this step is usually conducted under an anhydrous condition, under warming or heating in a conventional solvent such as benzene, dimethylsulfoxide, N,N-dimethylacetamide, tetrahydrofuran, acetonitrile, methylen chloride, ethylacetate, diethyl ether, methylethylketone, pyridine, or any other solvent which does not adversely influence to the reaction under an anhydrous condition.

In case that a phosphoryl azide of the formula (V) is used as an azide compound, the reaction is conducted under anhydrous condition throughout the reaction so that the isocyanate (III) can be obtained by one batch of reaction of a carboxylic acid (IV) and a phosphoryl azide (V), i.e. without isolation of an intermediary product of the formula (VI) as shown by the following reaction scheme and explained in details in the following.

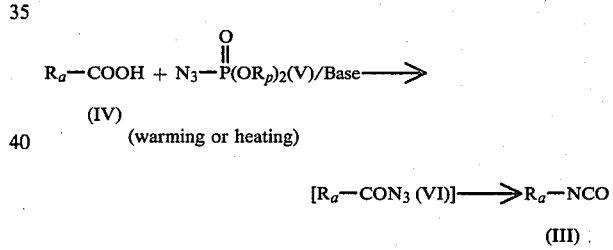

wherein Ra is as defined before and $R_p$ is lower alkyl or aryl.

In the above definition for $R_p$, preferred "lower alkyl" may be straight or branched C1 to C4 lower alkyl such as methyl, ethyl, propyl, isopropyl or butyl and the like, and preferred "aryl" may be phenyl or the like.

The isocyanate (III) is prepared in one batch step by reacting an acid of the formula (IV) with a phosphoryl azide of the formula (V) in the presence of a base.

The preferred phosphoryl azide (V) may include di(lower)alkylphosphoryl azide (e.g. dimethylphosphoryl azide, diethylphosphoryl azide, etc.) and diarylphosphoryl azide (e.g. diphenyl phosphoryl azide). These phosphoryl azide can be prepared by reacting the corresponding phosphoryl halide (e.g. dimethylphosphoryl chloride, diethylphosphoryl chloride, diphenylphosphoryl chloride, etc.) with sodium azide according to the method as described in the literature, for example, J. Org. Chem., vol. 27, page 4255, J. Amer. Chem. Soc., vol. 94, page 6203.

Preferred base may be an organic tertiary amine such as trialkylamine (e.g. trimethylamine, triethylamine, etc.), dialkylarylamine (e.g. N,N-dimethylaniline, etc.)

or the like, a nitrogen heterocyclic compound (e.g. pyridine, picoline, N-methylpyrrolidine, N-methylpiperidine, N-methylmorpholine, etc.) and the like.

The reaction of this one batch step is usually conducted under warming or heating in a conventional solvent is exemplified in the afore-mentioned Step 2 whose reaction is conducted under anhydrous condition.

As to the reaction, it is understood that the reaction of this step may proceed at first to produce the acid azide of the formula (VI) and then by thus produced acid azide (VI) is rearranged into the isocyanate (III) according to so-called Curtius rearrangement under the reaction conditions as employed.

The isocyanate (III) produced according to the above methods can be isolated from the reaction mixture by a conventional method. In this respect, it is to be noted that said reaction mixture per se comprising the isocyanate (III) and, in some case, the acid azide (VI) can also be used directly in the Process 1 as it is, i.e. without any isolation of the isocyanate, and in case that reaction mixture per se comprising the acid azide (VI) also is used in the above Process 1, said acid azide may be rearranged into the isocyanate (III) in reaction conditions of the Process 1 and the latter (III) may react with the 5-fluorouracil (II) to provide the 5-fluorouracil derivatives (I).

Particulars of the methods for the preparation of the isocyanate (III) as explained above will be exemplified in the working Examples hereinafter.

The carboxylic acid (IV) to be used in this process include known and novel compounds.

Preparation of the known compounds are referred to the following bibliography, i.e.

BEILSTEIN (4. Auflage, Gesamtregister) Sachregister für Band 17 U. 18 F-Z, page 1413–1418 (1977).
Chemische Berichte vol. 101, page 564–573 (1968),
Chemical Abstrate, vol. 65, 16975d.

Some representative particulars of the novel ones can be prepared according to the method as described in the working Examples and the others also can be prepared in the similar manner thereto. Some references of their preparations will generally be illustrated as follows.

Reference (1)

Preparation of a cyano(lower)alkylthio(lower)alkanoic acid [$R_a$—COOH, wherein $R_a$ is cyano(lower)alkylthio(lower)alkyl group]: cyano(lower)alkylthio(lower)alkanoic acid can be prepared by reacting cyano(lower)alkyl halide [e.g. cyano(lower)alkyl chloride, cyano(lower)alkyl bromide, etc.] with mercapto(lower)alkanoic acid. This reaction may be preferably conducted in the presence of conventional alkaline catalyst.

Especially, cyanoethylthio(lower)alkanoic acid can be prepared by reacting acrylonitrile with mercapto(lower)alkanoic acid (e.g. thioglycolic acid) as shown in the following reaction scheme:
$NC—CH=CH_2 + HS.CH_2COOH$
$NCCH_2CH_2SCH_2COOH$.

Reference (2)

Mono(lower)alkyl ester of 5-norbornen-2,3-dicarboxylic acid ($R_a$—COOH, wherein $R_a$ is (lower)alkoxycarbonylnorbornenyl): Mono(lower)alkyl ester of 5-norbornen-2,3-dicarboxylic acid can be prepared by reacting 5-norbornen-2,3-dicarboxylic anhydride with lower alkanol. This reaction is preferably conducted under heating. Particularly, the working example is to be referred to Example Nos. 23, 40, 41 and 44.

Reference (3)

Mono(lower)alkyl ester of norbornane-2,3-dicarboxylic acid ($R_a$—COOH, wherein $R_a$ is (lower)alkoxycarbonylnorbornyl): Mono(lower)alkyl ester of norbornane-2,3-dicarboxylic acid may be prepared by hydrogenating mono(lower)alkylester of 5-norbornene-2,3-dicarboxylic acid by a conventional manner. Particularly, the working example is to be referred to Example Nos. 24, 35, 36 and 37.

Reference (4)

3-[N,N-di(lower)alkylcarbamoyl]-5-norbornene-2-carboxylic acid [$R_a$—COOH, wherein $R_a$ is [N,N-di(lower)alkylcarbamoyl]norbornenyl]: 3-[N,N-di(lower)alkylcarbamoyl]-5-norbornene-2-carboxylic acid may be prepared by reacting 5-norbornene-2,3-dicarboxylic anhydride with di(lower)alkyl amine. This reaction is preferably conducted under heating. Particularly, the working example No. is to be referred to Example No. 39.

Reference (5)

3-[N,N-di(lower)alkylcarbamoyl]-5-norbornane-2-carboxylic acid $R_a$—COOH, wherein $R_a$ is: ]N,N-di(lower)alkylcarbamoyl]norbornyl]: 3-[N,N-di(lower)alkylcarbamoyl]-5-norbornane-2-carboxylic acid may be prepared by hydrogenating 3-[N,N-di(lower)alkylcarbamoyl]-5-norbornene-2-carboxylic acid by a conventional manner. Particularly, the working example No. is to be referred to Example No. 39.

Reference (6)

3-(lower)alkoxycarbonylbicyclo[2.2.2]octene-2-carboxylic acid [$R_a$—COOH, wherein $R_a$ is (lower)alkoxycarbonylbicyclo[2.2.2]octenyl]: 3-(lower)alkoxycarbonylbicyclo[2.2.2]octene-2-carboxylic acid may be prepared from D,L-5-bicyclo[2.2.2]-octene-2,3-dicarboxylic acid anhydride substantially in the similar method to that of preparing 3-(lower)alkoxycarbonylnorbornene-2,3-dicarboxylic acid. Particularly, the working example No. is to be referred to Example No. 49.

Reference (7)

3-(lower)alkoxycarbonylbicyclo[2.2.2]octane-2-carboxylic acid [$R_a$—COOH, wherein $R_a$ is: (lower)alkoxycarbonylbicyclo[2.2.2]octyl]: 3-(Lower)alkoxycarbonylbicyclo[2.2.2]octane-2-carboxylic acid may be prepared from 3-(lower)alkoxycarbonylbicyclo[2.2.2]octene-2-carboxylic acid substantially in the similar method to that of preparing D,L-3-(lower)alkoxycarbonylnorbornane-2-carboxylic acid. Particularly, the working example is to be referred to Example No. 49.

Process 2

The object compound (Ic) can be prepared by eliminating the amino protective group of the compound (Ib) as shown in the following scheme:

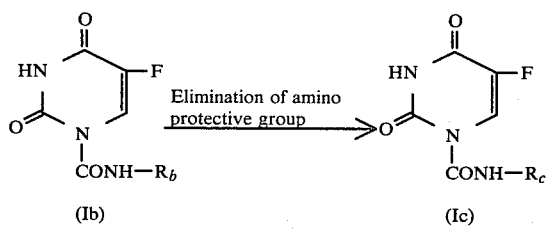

(Ib) → (Ic) Elimination of amino protective group wherein
R_b is bridged alicyclic group which has protected amino;
  substituted lower alkyl group, the substituent being selected from bridged alicyclic group, which has protected amino, and protected amino; or
  substituted lower alkenyl group, the substituent being selected from bridged alicyclic group, which has protected amino, and
R_c is bridged alicyclic group which has amino;
  substituted lower alkyl group, the substituent being selected from bridged alicyclic group, which has amino, and amino; or
  substituted lower alkenyl group, the substituent being selected from bridged alicyclic group, which has amino.

As to the definitions for R_b and R_c, particulars thereof are the same as the corresponding particulars explained and illustrated hereinabove for the corresponding definitions for R and so are to be referred to the explanation made hereinabove. Further, particulars of "protected amino" in the definitions for R_b are the same as those of "protected amino" explained hereinabove for the substituent of both of "bridged alicyclic group" and "substituted alkyl group" for R.

The elimination reaction of this process may be conducted in accordance with a conventional hydrolysis method, preferably under acidic condition.

Suitable acid to be used in acidic hydrolysis may include an organic or inorganic acid such as formic acid, trifluoroacetic acid, benzenesulfonic acid, p-toluenesulfonic acid, hydrochloric acid, hydrobromic acid, sulfuric acid, cation-exchange resin, and the like. Preferable acid is the one which can easily be separated out from the reaction mixture by a conventional manner such as neutralization or distillation under reduced pressure, for example, formic acid, trifluoroacetic acid, hydrochloric acid or the like. The acid suitable for the reaction can be selected in consideration of the chemical property of the starting compound and the product as well as the kind of the amino protective group to be eliminated. The acidic hydrolysis can be conducted in the presence or absence of a solvent.

Suitable solvent may be a conventional organic solvent, water or a mixture thereof, which does not adversely influence this reaction. Particularly, when the hydrolysis is conducted with trifluoroacetic acid, the reaction may be accelerated by addition of anisole.

The reaction temperature is not critical and may optionally be selected in consideration of the chemical property of the compound (Ib) and objective compound (Ic) as well as the kind of the amino protective group and the method to be applied, and the reaction is preferably carried out under a mild condition such as under cooling, at ambient temperature or slightly elevated temperature.

Process 3

The object compound (I_e) can also be prepared by hydrolyzing the compound (I_d) as shown in the following scheme:

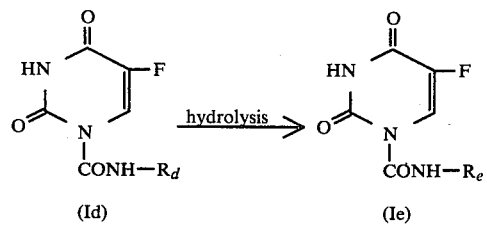

(Id) → (Ie) hydrolysis wherein
R_d is bridged alicyclic group, which has esterified carboxy;
  substituted lower alkyl group, the substituent being selected from bridged alicyclic group, which has esterified carboxy, and esterified carboxy; or
  substituted alkenyl group, the substituent being selected from bridged alicyclic group, which has esterified carboxy, and
R_e is bridge alicyclic group, which has carboxy; substituted lower alkyl group, the substituent being selected from bridged alicycic group, which has carboxy, and carboxy; or substituted alkenyl group, the substituent being selected from bridged alicyclic group, which has carboxy.

As to the definitions for R_d and R_e, particulars thereof are the same as the corresponding particulars explained and illustrated hereinbove for the corresponding definitions for R and so are to be referred to the explanation made hereinabove. Further, particulars of "esterified carboxy" in the definitions for R_d are the same as those of "esterified carboxy" explained hereinabove for the substituent of both of "bridged alicyclic group" and "substituted alkyl group" for R.

The hydrolysis of this process may be conducted in accordance with a conventional acidic hydrolysis.

Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound and the product as well as the kind of the alkoxycarbonyl group to be hydrolyzed. The acidic hydrolysis can be conducted in the presence or absence of a solvent.

Suitable solvent may be a conventional organic solvent, water or a mixture thereof, which does not adversely influence this reaction. Particularly, when the hydrolysis is conducted with trifluoroacetic acid, the reaction may be accelerated by addition of anisole.

The reaction temperature is not critical and may optionally be selected in consideration of the chemical property of the compound (Ib) and objective compound (I″) as well as the kind of alkoxycarbonyl group and the method to be applied, and the reaction is preferably carried out under a mild condition such as under cooling, at ambient temperature or slightly elevated temperature.

The object compounds (I) of this invention and pharmaceutically acceptable salts thereof exhibit strong antitumor activity, and are useful as an antitumor agent for therapeutical treatment in human being and animals.

For therapeutical administration, the 5-fluorouracil derivatives (I) or their pharmaceutically acceptable salts of this invention may be used in the form of pharmaceutical preparation which comprises said compound, as an active ingredient, in admixture with a pharmaceutically acceptable carrier such as an organic or inorganic solid or liquid excipient suitable for the oral or parentical administration. If desired, there may be included auxiliary substances, stabilizing agents, wetting or emulsifying agents, buffers and other commonly used additives in addition to the above exemplified excipitent. The pharmaceutical preparation may be prepared in solid form such as capsule, tablet, dragee, granule or suppository, or in liquid form such as solution, suspension or emulsion.

While the dosage of the compound of this invention may vary depending upon the age and/or the conditions of a patient, an average single dose of about 100 mg., 200 mg., 400 mg. and 1600 mg. of the compounds according to this invention may be effective for treating of tumors in human being and animals. In general amounts between about 200 mg. and about 4,000 mg. or even more may be administered to the patient per day.

Test data on antitumor activity or some representative compounds of this invention are shown below in order to show the utility of this invention.

Test Method

Male and female $BDF_1$ mice, aged more than 6 weeks, weighing more than 18 g. in male and more than 17 g. in female, were used in this experiment. Lymphocytic Leukemia (P388 or L 1210 was transferred every 6 or 7 days in DBA/2 mice by intraperitoneal inoculation of ascites cells. Test compounds were dissolved in aqueous methyl cellulose solution. In this experiment, after 24 hours of the inoculation of leukemia cells to the test mice, the test compound was administered orally in doses of 10, 32, 100, 180, 320 and 560 mg./kg. respectively in each medicated group (aqueous methyl cellulose only in the control group) once a day for 4 days. Antitumor activity of the test compounds was evaluated by the increase in life-span over control (ILS=T/C×100−100) in leukemias, wherein T is median survival time (MST) of the medicated group, and C is median survival time of control group.

Test Result

The test results are shown in the following tables 1-3.

The data shows that objective compounds have strong anti-tumor activity and little or no toxic effect.

TABLE 1

Antitumor activity of test compounds against Lymphocytic Leukemia P388 by oral administration

| Test compounds (No. of Examples) | No. of mice | Daily dose (mg./kg.) | Toxic death | MST (days) | ILS (%) | Weight change (g.) day 1 to day 4 |
|---|---|---|---|---|---|---|
| 11 | 7 | 180 | 0 | 16.0 | 46 | −0.2 |
| 17 | 7 | 180 | 0 | 14.0 | 27 | −0.6 |
| 26 | 7 | 180 | 0 | 15.0 | 36 | −1.0 |
| Control | 16 | 0 | 0 | 11.0 | — | +1.2 |
| 22 | 8 | 180 | 0 | 12.5 | 32 | −0.3 |
| 24 | 8 | 180 | 0 | 16.0 | 68 | +0.3 |
| Control | 10 | 0 | 0 | 9.5 | — | +2.2 |
| 29 | 10 | 100 | 0 | 15.0 | 50 | −0.2 |
| 30 | 10 | 100 | 0 | 14.0 | 40 | 0 |
| 33 | 10 | 100 | 0 | 13.0 | 30 | −0.4 |
| 35 | 10 | 100 | 0 | 14.0 | 40 | +0.2 |
| Control | 10 | 0 | 0 | 10.0 | — | +1.3 |

TABLE 2

Antitumor activity of test compounds against Lymphocytic Leukemia P388 and Lymphocytic Leukemia L 1210 by oral administration

| Test Compounds (No. of examples) | Daily dose (mg./kg.) | P388 ILS (%) | P388 Index* | L 1210 ILS (%) | L 1210 Index* |
|---|---|---|---|---|---|
| 1 | 560 | 20 | + | 47 | + |
|  | 320 | 40 | + | 47 | + |
|  |  | 35 | + |  |  |
|  |  | 10 | − |  |  |
|  | 180 | 50 | ++ |  |  |
|  |  | 35 | + |  |  |
|  | 100 | 50 | ++ | 14 | − |
|  |  | 40 | + |  |  |
|  |  | 30 | + |  |  |
|  | 32 | 20 | + |  |  |
|  | 10 | 10 | − |  |  |
| 2 | 560 | 10 | − |  |  |
|  | 320 | 25 | + | 89 | ++ |
|  |  | 10 | − |  |  |
|  | 180 | 44 | + |  |  |
|  |  | 25 | + |  |  |
|  | 100 | 55 | ++ | 26 | + |
|  |  | 20 | + |  |  |
|  | 32 | 20 | + | 5 | − |
|  | 10 | 10 | − |  |  |
| 15 | 560 | 0 | − | 31 | + |
|  | 320 | 40 | + | 17 | − |
|  |  | 40 | + |  |  |
|  | 180 | 33 | + |  |  |
|  |  | 25 | + |  |  |
|  | 100 | 10 | − | 1 | − |
|  |  | 10 | − |  |  |
| 24 | 560 | 0 | − |  |  |
|  | 320 | 10 | − | 60 | ++ |
|  | 180 | 68 | ++ |  |  |
|  | 100 | 40 | + | 17 | − |
|  | 32 | 15 | − | 2 | − |
|  | 10 | 10 | − |  |  |

*Index: <20 −, ≧20 +, ≧50 ++

TABLE 3

Antitumor activity of test compounds against Lymphocytic Leukemia P388 by oral administration

| Test compounds (No. of Examples) | Daily dose (mg./kg.) | ILS (%) | Weight change (g.) day 1 to day 4 |
|---|---|---|---|
| 3 | 180 | 44 | −0.1 |
| 34 | 100 | 27 | +0.8 |
| 36 | 100 | 33 | −0.5 |
| 37 | 100 | 23 | +0.8 |
| 40 | 100 | 32 | +0.6 |
| 41 | 100 | 52 | −0.7 |
| 42 | 100 | 24 | −0.4 |
| 43 | 100 | 27 | +0.6 |
| 44 | 100 | 48 | −0.8 |
| 45 | 100 | 38 | −0.5 |
| 46 | 100 | 27 | −1.6 |

TABLE 3-continued

| Antitumor activity of test compounds against Lymphocytic Leukemia P388 by oral administration | | | |
|---|---|---|---|
| Test compounds (No. of Examples) | Daily dose (mg./kg.) | ILS (%) | Weight change (g.) day 1 to day 4 |
| 49 | 100 | 36 | −1.3 |

The following Examples are given for the purpose of illustrating the present invention in more detail.

EXAMPLE 1

1-[N-(1-Adamantylmethyl)carbamoyl]-5-fluorouracil

A solution of diphenylphosphoryl azide [$N_3 \cdot PO(OC_6H_5)_2$] (5.50 g) in dry benzene (10 ml) and a solution of triethylamine (2.02 g) in dry benzene (10 ml) were added to a solution of 2-(1-adamantyl)acetic acid (3.88 g) in dry benzene (10 ml) with stirring at ambient temperature. The clear solution was stirred for 30 minutes at 80° C. to give a solution comprising 1-adamantylmethyl isocyanate (IR: 2270 cm$^{-1}$).

To the above solution of 1-adamantylmethyl isocyanate was added a solution of 5-fluorouracil (2.60 g) in N,N-dimethylacetamide (20 ml) at 80° C. and stirred for further 3 hours at the same temperature. The resultant mixture was diluted with ethyl acetate (200 ml), washed with water (each 30 ml., 3 times), dried over magnesium sulfate, treated with activated charcoal, filtered and evaporated in vacuo. The residue was recrystallized from diethyl ether to give 1-[N-(1-adamantylmethyl)-carbamoyl]-5-fluorouracil (1.85 g), as colorless crystalline powder.

m.p. 175°–176° C.

N.M.R. (CDCl$_3$) (ppm): 1.40 to 1.80 (12H, m), 1.80 to 2.2 (3H, m), 3.67 (2H, d, J=6 Hz), 8.47 (1H, d, J=7 Hz), 9.0 to 9.4 (1H, broad), 9.5 to 9.9 (1H, broad).

EXAMPLE 2

1-[N-(2-Norbornylmethyl)carbamoyl]-5-fluorouracil

The reaction of 2-norbornylacetic acid and diphenylphosphoryl azide in a solution of triethylamine and benzene provided a solution comprising 2-norbornylmethyl isocyanate (I.R.: 2270 cm$^{-1}$), which was reacted with 5-fluorouracil to provide 1-[N-(2-norbornylmethyl)carbamoyl]-5-fluorouracil substantially in the similar method to that of Example 1.

m.p. 165°–165.5° C. (recrystallized from ethyl acetate).

N.M.R. (DMSO-d$_6$) (ppm): 0.83 to 1.90 (8H, m), 2.0 to 2.30 (2H, m), 2.9 to 3.50 (3H, m), 8.37 (1H, d, J=8 Hz), 9.18 (1H, t, J=6 Hz), 11.4 (1H, broad).

EXAMPLE 3

1-[N-(2-Ethoxyethyl)carbamoyl]-5-fluorouracil

A solution of diphenylphosphoryl azide [$N_3 \cdot PO(OC_6H_5)_2$] (5.50 g.) in dry benzene (10 ml.) and a solution of triethylamine (2.02 g.) in dry benzene (10 ml.) were added to a solution of 3-ethoxypropionic acid (2.36 g.) in dry benzene (10 ml.) with stirring at ambient temperature. The clear solution was stirred for 30 minutes at 80° C. to give a solution comprising 2-ethoxyethyl isocyanate.

To the above solution of 2-ethoxyethyl isocyanate was added a solution of 5-fluorouracil (2.60 g.) in N,N-dimethylacetamide (20 ml.) at 80° and stirred for further 3 hours at the same temperature. The resultant mixture was diluted with ethyl acetate (200 ml.), washed with saturated sodium chloride aqueous solution (each 30 ml., 2 times), dried over magnesium sulfate, treated with activated charcoal, filtered and evaporated in vacuo. The residue was recrystallized from ethyl acetate to give 1-[N-(2-ethoxyethyl)carbamoyl]-5-fluorouracil (1.82 g.).

m.p. 134°–135° C. (recrystallized from ethyl acetate).

N.M.R. (CDCl$_3$) (ppm): 1.23 (3H, t, J=7 Hz), 3.40 to 3.87 (6H, m), 8.45 (1H, d, J=7 Hz), 9.27 (1H, broad), 9.63 (1H, broad).

EXAMPLE 4

1-[N-(2-acetylethyl)carbamoyl]-5-fluorouracil

A solution of diphenylphosphoryl azide [$N_3 \cdot PO(OC_6H_5)_2$](5.25 g.) in dry benzene (10 ml.) and a solution of triethylamine (2.0 g.) in dry benzene (10 ml.) were added to a solution of 3-acetylpropionic acid (2.32 g.) in dry benzene (10 ml.) with stirring at ambient temperature. The clear solution was stirred for 30 minutes at 50° C. to give a solution comprising 2-acetylethyl isocyanate.

To the above solution of 2-acetylethyl isocyanate was added a solution of 5-fluorouracil (2.60 g.) in N,N-dimethylacetamide (15 ml.) at 80° C. and stirred for further 5 hours at the same temperature. The resultant mixture was diluted with ethyl acetate (200 ml.), washed with water (each 30 ml., 3 times), dried over magnesium sulfate, treated with activated charcoal, filtered and evaporated in vacuo. The residue was recrystallized from ethyl acetate to give 1-[N-(2-acetylethyl)carbamoyl]-5-fluorouracil (439 mg.).

m.p. 158°–159° C. (recrystallized from ethyl acetate).

N.M.R. (DMSO-d$_6$) (ppm): 2.13 (3H, s), 2.73 (2H, t, J=6 Hz), 3.45 (2H, q, J=6 Hz), 8.37 (1H, d, J=8 Hz), 9.2 (1H, t, J=6 Hz), 12.0 to 12.5 (1H, broad).

EXAMPLE 5

1-[N-[2-(N′,N′-Diethylcarbamoyl)ethyl]carbamoyl]-5-fluorouracil

The reaction of 3-(N,N-diethylcarbamoyl)propionic acid and diphenylphosphoryl azide in a solution of triethylamine and benzene provided a solution comprising 2-(N′,N′-diethylcarbamoyl)ethyl isocyanate (I.R.: 2290 cm$^{-1}$), which was reacted with 5-fluorouracil to provide 1-[N-[2-(N′,N′-diethylcarbamoyl)ethyl]carbamoyl]-5-fluorouracil substantially in the similar method to that of Example 4.

m.p. 146°–147° C. (crystallized from ethyl acetate).

N.M.R. (DMSO-d$_6$) (ppm): 0.87 to 1.30 (6H, m), 2.5 to 2.8 (2H, m), 3.06 to 3.76 (6H, m), 8.43 (1H, d, J=8 Hz), 9.37 (1H, t, J=6 Hz)

EXAMPLE 6

1-[N-[2-(N′,N′-Dipropylcarbamoyl)ethyl]carbamoyl]-5-fluorouracil

The reaction of 3-(N,N-dipropylcarbamoyl)propionic acid and diphenylphosphoryl azide in a solution of triethylamine and benzene provided a solution comprising 2-(N′,N′-dipropylcarbamoyl)ethyl isocyanate (I.R.: 2280 cm$^{-1}$), which was reacted with 5-fluorouracil to provide 1-[N-[2-(N′,N′-dipropylcarbamoyl)ethyl]carbamoyl]-5-fluorouracil substantially in the similar method to that of Example 4.

m.p. 175°–176° C. (recrystallized from ethyl acetate).

N.M.R. (DMSO-d$_6$) (ppm): 0.67 to 1.10 (6H, m), 1.2 to 1.9 (2H, m), 3.0 to 3.83 (6H, m), 8.37 (1H, d, J=8 Hz), 9.33 (1H, t, J=6 Hz).

EXAMPLE 7

1-[N-[3-(N',N'-Dipropylcarbamoy)propyl]carbamoyl]-5-fluorouracil

The reaction of 4-(N,N-dipropylcarbamoyl)butylic acid and diphenylphosphoryl azide in a solution of triethylamine and benzene provided a solution comprising 3-(N',N'-dipropylcarbamoyl)propyl isocyanate, which was reacted with 5-fluorouracil to provide 1-[N-[3-(N',N'-dipropylcarbamoyl)propyl]carbamoyl]-5-fluorouracil substantially in the similar method to that of Example 4.

m.p. 146°–146.5° C. (recrystallized from ethyl acetate).

N.M.R. (DMSO-d$_6$) (ppm): 0.6 to 1.0 (6H, m), 1.1 to 2.0 (6H, m), 2.25 (2H, d), 2.95 to 3.5 (6H, m), 8.67 (1H, d, J=8 Hz), 9.07 (1H, t, J=6 Hz), 12.25 (1H, s).

EXAMPLE 8

1-[N-[2-(N',N'-Diallylcarbamoyl)ethyl]carbamoyl]-5-fluorouracil

The reaction of 3-(N,N-diallylcarbamoyl)propionic acid and diphenylphosphoryl azide in a solution of triethyl amine and benzene provided a solution comprising 2-(N',N'-diallylcarbamoyl)ethyl isocyanate (I.R.: 2275 cm$^{-1}$), which was reacted with 5-fluorouracil to provide 1-[N-[2-(N',N'-diallylcarbamoyl)ethyl]carbamoyl]-5-fluorouracil substantially in the similar method to that of Example 4.

m.p. 126°–127° C. (recrystallized from ethyl acetate).

N.M.R. (DMSO-d$_6$) (ppm): 2.40 to 2.72 (2H, m), 3.36 to 3.64 (2H, m), 3.90 (4H, d, J=5 Hz), 4.92 to 5.3 (4H, m), 5.5 to 6.05 (2H, m), 8.36 (1H, d, J=8 Hz), 9.36 (1H, t, J=6 Hz).

EXAMPLE 9

1-[N-(2-Morpholinocarbonylethyl)carbamoyl]-5-fluorouracil

The reaction of 3-morpholinocarbonylpropionic acid and diphenylphosphoryl azide in a solution of triethyl amine and benzene provided a solution comprising 2-morpholinocarbonylethyl isocyanate, which was reacted with 5-fluorouracil to provide 1-[N-(2-morpholinocarbonylethyl)carbamoyl]-5-fluorouracil substantially in the similar method to that of Example 4.

m.p. 178°–180° C. (recrystallized from ethyl acetate).

N.M.R. (DMSO-d$_6$) (ppm): 2.3 to 2.8 (2H, m), 3.1 to 3.7 (10H, m), 8.38 (1H, d, J=8 Hz), 9.36 (1H, t, J=6 Hz).

EXAMPLE 10

1-[N-(2-Propylthioethyl)carbamoyl]-5-fluorouracil

A solution of diphenylphosphoryl azide [N$_3$.PO(OC$_6$H$_5$)$_2$] (8.25 g.) in dry benzene (10 ml.) and a solution of triethylamine (3.03 g.) in dry benzene (10 ml.) were added to a solution of 3-propylthiopropionic acid (4.44 g.) in dry benzene (10 ml.) with stirring at ambient temperature. The clear solution was stirred for 30 minutes at 70°–80° C. to give a solution comprising 2-propylthioethyl isocyanate (I.R.: 2260 cm$^{-1}$).

To the above solution of 2-propylthioethyl isocyanate was added a solution of 5-fluorouracil (2.60 g.) in N,N-dimethylacetamide (20 ml.) at 80° C. and stirred for further 8 hours at the same temperature. The resultant mixture was diluted with ethyl acetate (200 ml.), washed with water (each 30 ml., 3 times), dried over magnesium sulfate, treated with activated charcoal, filtered and evaporated in vacuo. The residue was recrystallized from ethyl acetate to give 1-[N-(2-propylthioethyl)carbamoyl]-5-fluorouracil.

m.p. 112°–114° C. (recrystallized from ethyl acetate).

N.M.R. (DMSO-d$_6$) (ppm): 0.95 (3H, t, J=8 Hz), 1.56 (2H, sex, J=8 Hz), 2.4 to 2.8 (4H, m), 3.36 to 3.64 (2H, m), 8.40 (1H, d, J=8 Hz), 9.36 (1H, t, J=6 Hz).

EXAMPLE 11

1-[N-[2-(2-Cyanoethylthio)ethyl]carbamoyl]-5-fluorouracil

The mixture of acrylonitrile (5.31 g.) and 3-mercaptopropionic acid (10.6 g.) was stirred for 1 day at ambient temperature and distilled under reduced pressure to give colorless liquid of 3-(2-cyanoethylthio)propionic acid (7.5 g.). B. p. 124°–126° C./10-13 mm Hg.

I.R. (Nujole): 2250, 1720 cm$^{-1}$.

The reaction of 3-(2-cyanoethylthio)propionic acid and diphenylphosphoryl azide in a solution of triethyl amine and benzene provided a solution comprising 2-(2-cyanoethylthio)ethyl isocyanate (I.R.: 2250 cm$^{-1}$), which was reacted with 5-fluorouracil to provide 1-[N-[2-(2-cyanoethylthio)ethyl]carbamoyl]-5-fluorouracil substantially in the similar method to that of Example 10.

m.p. 121°–123° C. (recrystallized from ethyl acetate).

N.M.R. (DMSO-d$_6$) (ppm): 2.07 (2H, t, J=7 Hz), 2.6 to 3.1 (2H, m), 3.1 to 3.8 (4H, m), 8.4 (1H, d, J=8 Hz), 9.33 (1H, t, J=6 Hz).

EXAMPLE 12

1-[N-(2-Phenylthioethyl)carbamoyl]-5-fluorouracil

The reaction of 3-phenylthiopropionic acid and diphenylphosphoryl azide in a solution of triethyl amine and benzene provided a solution comprising 2-phenylthioethyl isocyanate (I.R.: 2260 cm$^{-1}$), which was reacted with 5-fluorouracil to provide 1-[N-(2-phenylthioethyl)carbamoyl]-5-fluorouracil substantially in the similar method to that of Example 10.

m.p. 130°–133° C. (recrystallized from ethyl acetate).

N.M.R. (DMSO-d$_6$) (ppm): 2.7 to 3.7 (4H, m), 7.1 to 7.45 (5H, m), 8.38 (1H, d, J=8 Hz), 6.25 [nh]$^{*a)}$, 9.45 [h]$^{*b)}$ (1H, t, J=6 Hz; t, J=6 Hz), 11.7–12.4 (1H, broad)

(*a) [nh]; Non-hydrogen-bonded,
(*b) [h]; hydrogen-bonded

EXAMPLE 13

1-[N-(4-Pyridylmethyl)carbamoyl]-5-fluorouracil

Diphenylphosphoryl azide (5.5 g.) was added to a solution of 4-pyridyl acetic acid (2.74 g.) with stirring at ambient temperature. The clear solution was stirred for 30 minutes at 80° C. to give a solution comprising 4-pyridylmethyl isocyanate (I.R.: 2280 cm$^{-1}$).

To the above solution of 4-pyridylmethyl isocyanate was added 5-fluorouracil (2.60 g.) at 80° C. and stirred for 4 hours at the same temperature. The resultant mixture was evaporated in vacuo. The residue was washed with diethyl ether (3 times) and crystallized. The crystals were filtered and washed with a small amount of ethanol. To the washed crystals a small amount of pyridine was added, and the mixture was warmed to be dissolved and cooled to be recrystallized. The crystals were washed successively with ethyl acetate and diethyl ether to give 1-[N-(4-pyridylmethyl)carbamoyl]-5-fluorouracil (1.75 g.)

m.p. 195°-200° C. (dec.) (recrystallized from pyridine).

N.M.R. (DMSO-d$_6$) (ppm): 4.5 (2H, d, J=6 Hz), 7.2 to 7.85 (2H, m), 8.33 (1H, d, J=8 Hz), 8.4 to 8.65 (2H, m), 9.57 (1H, t, J=6 Hz), 11.2 to 13.0 (1H, broad)

EXAMPLE 14

1-[N-(2-Thienylmethyl)carbamoyl]-5-fluorouracil

The reaction of 2-thienylacetic acid and diphenylphosphoryl azide in a solution of triethyl amine and benzene provided a solution comprising 2-thienylmethyl isocyanate, which was reacted with 5-fluorouracil to provide 1-[N-(2-thienylmethyl)carbamoyl]-5-fluorouracil substantially in the similar method to that of Example 13.

m.p. 131°-132° C. (recrystallized from ethyl acetate).

N.M.R. (DMSO-d$_6$) (ppm): 4.38 (1H, d, J=6 Hz), 4.65 (1H, d, J=6 Hz), 6.9 to 7.5 (3H, m), 8.42 (1H, d, J=7 Hz), 9.66 (1H, t, J=6 Hz), 12.0 to 12.5 (1H, broad)

EXAMPLE 15

1-[N-[4-(1,2-Dithiolan-3-yl)butyl]carbamoyl]-5-fluorouracil

The reaction of 5-(1,2-dithiolan-3-yl)pentanoic acid and diphenylphosphoryl azide in a solution of triethyl amine and benzene provided a solution comprising 4-(1,2-dithiolan-3-yl)butyl isocyanate (I.R.: 2270 cm$^{-1}$), which was reacted with 5-fluorouracil to provide 1-[N-[4-(1,2-dithiolan-3-yl)butyl]carbamoyl]-5-fluorouracil substantially in the similar method to that of Example 13.

m.p. 126° C. (recrystallized from diethyl ether).

N.M.R. (CDCl$_3$) (ppm): 1.4 to 3.9 (13H, m), 8.52 (1H, d, J=7 Hz), 9.10 (1H, broad).

EXAMPLE 16

1-[N-[5-(2,5-dioxopyrrolidin-1-yl)pentyl]carbamoyl]-5-fluorouracil

The reaction of 6-[(2,5-dioxopyrrolidin-1-yl)hexanoic acid and diphenylphosphoryl azide in a solutuon of triethyl amine and benzene provided a solution comprising 5-(2,5-dioxopyrrolidin-1-yl)pentyl isocyanate, which was reacted with 5-fluorouracil to provide 1-[N-[5-(2,5-dioxopyrrolidin-1-yl)pentyl]carbamoyl]-5-fluorouracil substantially in the similar method to that of Example 13.

m.p. 142°-142.5° C. (recrystallized from ethyl acetate).

N.M.R. (DMSO-d$_6$) (ppm): 1.2 to 1.8 (6H, m), 2.63 (4H, s), 3.1 to 3.6 (4H, m), 8.40 (1H, d, J=8 Hz), 9.10 (1H, t, J=6 Hz).

EXAMPLE 17

1-[N-[2-trans-2-Furyl)ethenyl]carbamoyl]-5-fluorouracil

A solution of diphenylphosphoryl azide [N$_3$.PO(OC$_6$H$_5$)$_2$] (5.50 g.) in dry benzene (10 ml.) and a solution of triethyl amine (2.0 g.) in dry benzene (10 ml.) were added to a solution of trans-3-furylacrylic acid (2.76 g.) in dry benzene (10 ml.) with stirring at ambient temperature. The clear solution was stirred for 30 minutes at 80° C. to give a solution comprising 2-(2-furyl)ethenyl isocyanate (I.R.: 2150 cm$^{-1}$).

To the above solution of 2-(2-furyl)ethenyl isocyanate was added a solution of 5-fluorouracil (2.60 g.) in N,N-dimethylacetamide (15 ml.) at 80° C. and stirred for further 3 hours at the same temperature. The resultant mixture was diluted with ethyl acetate (200 ml.), washed with water (3 times), dried over magnesium sulfate, treated with activated charcoal, filtered and evaporated in vacuo. The residue was recrystallized from ethyl acetate to give 1-[N-[2-(trans-2-furyl)ethenyl]carbamoyl]-5-fluorouracil.

m.p. 215°-217° C. (dec.) (recrystallized from ethyl acetate).

N.M.R. (DMSO-d$_6$) (ppm): 5.95 (1H, d, J=15 Hz), 6.05 to 7.6 (4H, m), 7.7 (1H, d, J=7 Hz), 9.0 [h]*$^{b)}$, 8.4 [nh]*$^{a)}$ (1H, d, J=11 Hz; d, J=8 Hz), 10.7 to 11.7 (1H, broad)

(*a) [nh]; Non-hydrogen-bonded,
(*b) [nh]; Hydrogen-bonded

EXAMPLE 18

1-[N-[trans-2(2,6-Dimethoxyphenyl)ethenyl]carbamoyl]-5-fluorouracil

The reaction of 3-(2,6-methoxyphenyl)acrylic acid and diphenylphosphoryl azide in a solution of triethyl amine and benzene provided a solution comprising 2-(2,6-dimethoxyphenyl)ethenyl isocyanate (I.R.: 2150 cm$^{-1}$), which was reacted with 5-fluorouracil to provide 1-[N-[trans-2-(2,6-dimethoxyphenyl)ethenyl]carbamoyl]-5-fluororuacil substantially in the similar method to that of Example 17.

m.p. 193°-195° C. (recrystallized from ethyl acetate).

N.M.R. (DMSO-d$_6$) (ppm): 3.70 (3H, s), 3.78 (3H, s), 6.18 (1H, d, J=14 Hz), 6.5 to 7.1 (3H, m), 7.15 to 7.57 (1H, m), 7.77 (1H, d, J=7 Hz), 8.9 [h]*$^{b)}$, 8.37 [nh]*$^{a)}$ (1H, d, J=11 Hz; d, J=8 Hz), 10.8 to 11.7 (1H, broad).

*a) [nh]; Non-hydrogen-bonded
*b) [h]; Hydrogen-bonded

EXAMPLE 19

1-[N-(trans, trans-1,3-Pentadienyl)carbamoyl]-5-fluorouracil

A solution of diphenylphosphoryl azide [N$_3$.PO(OC$_6$H$_5$)$_2$] (5.50 g.) in dry benzene (10 ml.) and a solution of triethylamine (2.02 g.) in dry benzene (10 ml.) were added to a solution of 2,4-hexadienoic acid (2.24 g.) in dry benzene (10 ml.) with stirring at ambient temperature. The clear solution was stirred for 3 hours at 50° C. to give a solution comprising trans,trans,-1,3-pentadienyl isocyanate.

To the above solution of trans,trans-1,3-pentadienyl isocyanate was added a solution of 5-fluorouracil (2.6 g.) in N,N-dimethylacetamide (15 ml.) at 80° C. and stirred for 3 hours at the same temperature. The resultant mixture was diluted with ethyl acetate (100 ml.), washed with water (4 times), dried over magnesium sulfate, filtered and evaporated in vacuo. The residue was recrystallized from diethyl ether to give 1-[N-(trans,trans-1,3-pentadienyl)carbamoyl]-5-fluorouracil.

m.p. 163° C. (recrystallized from diethyl ether).

N.M.R. (DMSO-d$_6$) (ppm): 1.5 to 1.83 (3H, m), 5.13 to 7.0 (4H, m), 7.73 (1H, d, J=6 Hz), 8.37 [nh]$^{(*a)}$, 10.86 [h]$^{(*b)}$ (1H, d, J=8 Hz; d, J=10 Hz), 11.0 to 11.9 (1H, broad).

(*a) [nh]; Non-hydrogen-bonded
(*b) [h]; Hydrogen-bonded

EXAMPLE 20

1-[N-(3-t-Butoxycarbonylaminopropyl)carbamoyl]-5-fluorouracil

A solution of diphenyl phosphoryl azide [$N_3$·PO(OC$_6$H$_5$)$_2$] (5.50 g.) in dry benzene (10 ml.) and a solution of triethylamine (2.02 g.) in dry benzene (10 ml.) were added to a solution of 4-t-butoxycarbonylaminobutylic acid (4.06 g.) in dry benzene (10 ml.) with stirring at ambient temperature. The clear solution was stirred for 30 minutes at 80° C. to give a solution comprising 3-t-butoxycarbonylaminopropyl isocyanate (I.R.: 2280 cm$^{-1}$).

To the above solution of 3-t-butoxycarbonylaminopropyl isocyanate was added a solution of 5-fluorouracil (2.60 g.) in N,N-dimethylacetamide (20 ml.) at 80° C. and stirred for further 3 hours at the same temperature. The resultant mixture was diluted with ethyl acetate (200 ml.), washed with water (each 30 ml., 3 times), dried over magnesium sulfate, treated with activated charcoal, filtered and evaporated in vacuo. The residue was recrystallized from ethyl acetate to give 1-[N-(3-t-butoxycarbonylaminopropyl)carbamoyl]-5-fluorouracil.

I.R. (Nujol): 3250, 3100, 2930, 2850, 1760, 1720, 1680, 1490, 1430, 1310, 1280, 1240, 1200, 1175, 1125, 1070, 910, 860, 810, 770, 740, 720 cm$^{-1}$

EXAMPLE 21

1-[N-(5-t-Butoxycarbonylamino)pentyl)carbamoyl]-5-fluorouracil

The reaction of 6-t-butoxycarbonylaminohexanoic acid and diphenylphosphoryl azide in a solution of triethyl amine and benzene provided a solution comprising 5-t-butoxycarbonylaminopentyl isocyanate, which was reacted with 5-fluorouracil to provide 1-[N-(5-t-butoxycarbonylaminopentyl)carbamoyl]-5-fluorouracil substantially in the similar method to that of Example 20.

I.R. (Nujol): 3200, 3100, 3050, 2930, 2850, 1760, 1720, 1680, 1490, 1430, 1395, 1310, 1280, 1240, 1200, 1175, 1125, 1070, 910, 860, 810, 770, 760, 720 cm$^{-1}$

EXAMPLE 22

1-[N-[2-(trans-2-Thienyl)ethenyl]carbamoyl]-5-fluorouracil

The reaction of trans-3-(2-thienyl)acrylic acid and diphenylphosphoryl azide in a solution of triethyl amine and benzene provided a solution comprising 2-(2-thienyl)ethenyl isocyanate, which was reacted with 5-fluorouracil to provide 1-[N-[2-(trans-2-thienyl)ethenyl]carbamoyl]-5-fluorouracil substantially in the similar method to that of Example 17.

m.p. 163°–166° C. (dec.) (recrystallized from ethyl acetate).

N.M.R. (DMSO-$d_6$) (ppm): 6.28 (1H, d, J=14 Hz), 6.6 to 7.5 (4H, m), 7.75 (1H, d, J=6 Hz), 8.41 [nh]*$^{(a)}$, 9.0 [h]*$^{(b)}$ (1H, d, J=7 Hz; d, J=11 Hz), 10.5 to 12.0 (1H, broad).

(*a) [nh]; Non-hydrogen-bonded
(*b) [h]; Hydrogen-bonded

EXAMPLE 23

D,L-1-[N-(3-Methoxycarbonyl-5-norbornen-2-yl)carbamoyl]-5-fluorouracil

A mixture of 5-norbornen-2,3-dicarboxylic anhydride (24.6 g.) and methanol (68 g.) was heated to reflux for 8 hours and evaporated to dryness under reduced pressure. The oily residue was made solidified and dried to give D,L-5-norbornen-2,3-dicarboxylic acid monomethyl ester (29.0 g.), as powders.

N.M.R. (CDCl$_3$) (ppm): 1.33 to 1.66 (2H, m), 3.0 to 3.43 (4H, m), 3.57 (3H, s), 6.1 to 6.5 (2H, m), 10.12 (1H, s).

The reaction of D,L-5-norbornen-2,3-dicarboxylic acid monomethyl ester and diphenylphosphoryl azide in a solution of triethyl amine and benzene provided a solution comprising 3-methoxycarbonyl-5-norbornen-2-yl isocyanate, which was reacted with 5-fluorouracil to provide D,L-1-[N-3-(methoxycarbonyl-5-norbornen-2-yl)carbamoyl]-5-fluorouracil substantially in the similar method to that of Example 1.

m.p. 144°–145° C. (crystallized from ethyl acetate).

N.M.R. (DMSO-$d_6$) (ppm): 1.47 (2H, broad s), 3.12 (2H, broad s), 3.23 to 3.43 (1H, m), 3.5 (3H, s), 4.6 to 5.1 (1H, m), 6.07 to 6.6 (2H, m), 8.4 (1H, d, J=8 Hz), 9.09 (1H, d, J=9 Hz), 11.5 to 12.8 (1H, broad)

EXAMPLE 24

D,L-1-[N-(2-Methoxycarbonylnorborn-3-yl)carbamoyl]-5-fluorouracil

D,L-5-Norbornen-2,3-dicarboxylic acid monomethyl ester which was prepared in Example 23 (24.0 g.) was dissolved in ethanol (300 ml.), and hydrogenated over 10% palladium charcoal catalyst under hydrogen atmosphere of ordinary pressure at ambient temperature. The reaction mixture was filtrated and the filtrate was concentrated in vacuo. The oily residue was made solidified and dried to give D,L-norbornan-2,3-dicarboxylic acid monomethyl ester (24.3 g.), as powders.

I.R. (Nujol): 1730, 1700, 1435, 1420, 1360, 1330, 1310, 1300, 1290, 1255, 1240, 1210, 1190, 1120, 1080, 900, 740 cm$^{-1}$.

N.M.R. (DMSO-$d_6$) (ppm): 1.1 to 2.1 (6H, m), 2.33 to 2.7 (2H), 3.0 (2H, broad s), 3.53 (3H, s)

The reaction of D,L-norbornan-2,3-dicarboxylic acid monomethyl ester and diphenylphosphoryl azide in a solution of triethyl amine and benzene provided a solution comprising D,L-2-methoxycarbonylnorborn-3-yl isocyanate (I.R.: 2300 cm$^{-1}$), which was reacted with 5-fluorouracil to provide D,L-1-[N-(2-methoxycarbonylnorborn-3-yl)carbamoyl]-5-fluorouracil substantially in the similar method to that of Example 1.

m.p. 164°–165° C. (crystallized from ethyl acetate).

N.M.R. (DMSO-$d_6$) (ppm): 1.5 (6H, broad s), 2.33 to 2.67 (2H), 2.9 to 3.4 (1H, m), 3.6 (3H, s), 4.07 to 4.6 (1H, m), 8.4 (1H, d, J=8 Hz), 10.07 (1H, d, J=8 Hz), 12.3 (1H, broad s).

EXAMPLE 25

1-[N-(3-Aminopropyl)carbamoyl]-5-fluorouracil hydrochloride

Hydrogen chloride gas was introduced to the solution of 1-[N-[3-(t-butoxycarbonylamino)propyl]carbamoyl]-5-fluorouracil (5.1 g.) which was prepared in Example 20 in ethanol (30 ml.) until precipitates were appeared for 1 hour with stirring under cooling with ice. The reaction mixture was further stirred for 1 hour at ambient temperature, and diethyl ether (100 ml.) was added therein. The resultant crystalline precipitates were collected by filtration and were dried over phosphoric anhydride to give 1-[N-(3-aminopropyl)carbamoyl]-5-fluorouracil hydrochloride (1.5 g.).

m.p. 173°–174° C. (crystallized from diethyl ether).

N.M.R. (DMSO-d$_6$) (ppm): 1.43 to 2.17 (2H, m), 2.53 to 3.57 (4H, m), 8.27 (1H, d, J=8 Hz), 9.1 (1H, t, J=6 Hz), 12.27 (1H, broad).

EXAMPLE 26

1-[N-(5-Aminopentyl)carbamoyl]-5-fluorouracil hydrochloride

1-[N-(5-Aminopentyl)carbamoyl]-5-fluorouracil hydrochloride was prepared in substantially the similar method to that of Example 25 from 1-[N-[5-(t-butoxycarbonylamino)pentyl]carbamoyl]-5-fluorouracil which was prepared in Example 21.

m.p. 171°–172° C. (dec.) (crystallized from diethyl ether).

N.M.R. (DMSO-d$_6$) (ppm): 1.05 to 2.0 (6H, m), 2.5 to 3.1 (2H, m), 3.1 to 3.6 (2H, m), 8.4 (1H, d, J=8 Hz), 9.15 (1H, t, J=6 Hz), 12.37 (1H, broad).

EXAMPLE 27

1-[N-(2-Tetrahydrothienyl)carbamoyl]-5-fluorouracil

Thionyl chloride (16.5 g.) was added to 2-tetrahydrothiophenecarboxylic acid (12.2 g.) at ambient temperature and heated for 2 hours at 80° C. The reaction mixture was evaporated to dryness under reduced pressure and the residual oil was fractionated by distillation in vacuo to give 2-tetrahydrothiophenecarboxylic acid chloride (9.79 g.), (b.p. 46° C./1 mmHg).

N.M.R. (CDCl$_3$) (ppm): 1.8 to 2.6 (4H, m), 2.85 to 3.2 (2H, m), 4.15 to 4.4 (1H, m).

A solution of sodium azide (4.14 g.) in water (16 ml.) was added dropwise to a solution of 2-tetrahydrothiophenecarboxylic acid chloride (9.60 g.) in diethyl ether (24 ml.) with stirring under ice-cooling and stirred for further 15 minutes at the same temperature. After the mixture was stirred for 1 hour at ambient temperature, nitrogen gas was introduced to remove off diethyl ether. The resultant mixture was extracted with diethyl ether (50 ml.). The extracts were washed with water, dried over magnesium sulfate and concentrated in vacuo to give oily 2-tetrahydrothiophenecarboxylic acid azide (8.63 g.).

I.R. (firm): 2950, 2860, 2150, 1710, 1680, 1590, 1310, 1160–1240, 1080, 900 cm$^{-1}$.

A solution of 2-tetrahydrothiophenecarboxilic acid azide (8.5 g.) in benzene (20 ml.) was stirred at 70° C. for 4 hours under nitrogen atmosphere. The reaction mixture was evaporated to dryness under reduced pressure to give oily 2-tetrahydrothienyl isocyanate (7.3 g.).

I.R. (firm): 2950, 2880, 2250, 1680, 1590, 1440, 1310, 1190–1240, 900 cm$^{-1}$.

A solution of 5-fluorouracil (2.6 g.) in N,N-dimethylacetoamide (10 ml.) was added to oily 2-tetrahydrothienyl isocyanate (3.1 g.). The mixture was stirred at 50° C. for 8 hours and concentrated in vacuo. The residue was treated with water (80 ml.) to give crystalline precipitates, which were collected by filtration and dried over phosphoric anhydride to give 1-[N-(2-tetrahydrothienyl)carbamoyl]-5-fluorouracil (3.68 g.); pale yellow crystalline powder.

m.p. 148° C. (recrystallized from diethyl ether).

N.M.R. (DMSO-d$_6$) (ppm): 1.8 to 2.2 (4H, m), 2.7 to 3.2 (2H, m), 5.32 to 5.55 (1H, m), 8.30 (1H, d, J=8 Hz), 9.40 (1H, d, J=8 Hz), 12.35 (1H, broad s).

EXAMPLE 28

1-[N-(4-Chlorophenyl)carbamoyl]-5-fluorouracil

A solution of 5-fluorouracil (2.6 g.) in pyridine (25 ml.) was added to 4-chlorophenyl isocyanate (3.07 g.) and the solution was stirred at 80° C. for 4 hours. The resultant solution was allowed to stand overnight in a refrigerator. The crystalline precipitates were collected by filtration, washed successively with ethyl acetate, diethyl ether, and then dried to give 1-[N-(4-chlorophenyl)carbamoyl]-5-fluorouracil (3.30 g.); colorless crystalline powder.

m.p. over 260° C. (recrystallized from pyridine).

N.M.R. (DMSO-d$_6$) (ppm): 7.2–7.7 (4H, m), 7.73 (1H, d, J=6 Hz), 8.80 (1H, t, J=7 Hz), 10.5 to 11.67 (1H, broad).

EXAMPLE 29

1-[N-(2-Norbornyl)carbamoyl]-5-fluorouracil

The reaction of 2-norbornanecarboxlic acid and diphenylphosphoryl azide in a solution of triethylamine and benzene provided a solution comprising 2-norbornyl isocyanate (I.R.: 2270 cm$^{-1}$), which was reacted with 5-fluorouracil to provide 1-[N-(2-norbornyl)carbamoyl]-5-fluorouracil substantially in the similar method to that of Example 1.

m.p. 252°–255° C. (recrystallized from ethyl acetate).

N.M.R. (DMSO-d$_6$) (ppm): 1.0 to 1.67 (8H, broad s), 1.80 to 2.43 (2H, m), 3.33 to 3.73 (1H, m), 8.43 (1H, d, J=8 Hz), 9.33 (1H, d, J=7 Hz).

EXAMPLE 30

1-[N-[3-(2-Thienyl)propyl]carbamoyl]-5-fluorouracil

Diphenyl phosphoryl azide [N$_3$.PO(OC$_6$H$_5$)] (9.08 g.) was added dropwise to a solution of 4-(2-thienyl)butyric acid (5.53 g.) in dry pyridine (25 ml.) and stirred for one hour at 100° C. to give a solution comprising 3-(2-thienyl)propyl isocyanate (I.R.: 2260 cm$^{-1}$).

5-Fluorouracil (3.30 g.) was added to the solution of 3-(2-thienyl)propyl isocyanate and stirred at 100° C. for 2 hours. The resultant mixture was evaporated to dryness under reduced pressure. The residue was dissolved in ethyl acetate, washed with water, dried over magnesium sulfate, filtered and evaporated under reduced pressure. The residue was recrystallized from ethanol to give colorless plate 1-[N-[3-(2-thienyl)propyl]carbamoyl]-5-fluorouracil (2.3 g.).

M.p. 131°–133° C.

N.M.R. (DMSO-d$_6$) (ppm): 1.90 (2H, quintet, J=7 Hz) 2.87 (2H, t, J=7 Hz), 3.37 (2H, qualtet, J=7 Hz), 6.83 to 7.07 (2H, m), 7.20 to 7.40 (1H, m), 8.40 (1H, d, J=8 Hz), 9.18 (1H, t, J=6 Hz), 12.22 (1H, s)

EXAMPLE 31

1-[N-(3-tert-Butoxycarbonylpropyl)carbamoyl]-5-fluorouracil

Glutaric anhydride (11.41 g.) was added portion-wise to a solution of potassium tert-butoxide (14.02 g.) in tetrahydrofuran (100 ml.) at ambient temperature. After the exothermic reaction was ceased, the reaction mixture was stirred at 40° C. for 15 minutes. Tetrahydrofuran was distilled off under reduced pressure. The residue was dissolved in water. After ethyl acetate was added, the solution was adjusted to pH 9 with aqueous potassium carbonate solution under ice-cooling. The separated water layer was washed with ethyl acetate, treated with activated charcoal, overlapped with ethyl acetate, and then adjusted to pH 4.0 with 10% hydrochloric acid under ice-cooling. The ethyl acetate layer was dried over magnesium sulfate, treated with activated charcoal, filtered and concentrated under reduced pressure to give glutaric acid mono-tert-butyl ester (10 g.).

N.M.R. (CDCl$_3$) (ppm): 1.43 (9H, s), 1.67 to 2.67 (6H, m)

Diphenylphosphoryl azide (12.25 g.) was added dropwise to a solution of glutaric acid mono-tert-butyl ester (8.38 g.) in dry pyridine (37 ml.) and stirred at 90° C. for 40 minutes to give 3-tert-butoxycarbonylpropyl isocyanate (I.R.: 2270 cm$^{-1}$).

5-Fluorouracil (4.83 g.) was added to the solution and stirred at 90° C. for 3 hours. The resultant mixture was evaporated under reduced pressure. The residue was dissolved in ethyl acetate and washed with dilute hydrochloric acid and water. Ethyl acetate layer was dried over magnesium sulfate, treated with activated charcoal, filtered and concentrated under reduced pressure to give the crystals of 1-[N-(3-tert-butoxycarbonylpropyl)carbamoyl]-5-fluorouracil. Recrystallization from ethanol gave the pure compound (411 mg.).

N.M.R. (DMSO-d$_6$) (ppm): 1.43 (9H, s), 1.57 to 2.33 (4H, m), 3.57 (2H, m), 8.68 (1H, d, J=8 Hz), 11.00 (1H, broad), 14.40 (1H, broad)

EXAMPLE 32

1-[N-(3-Carboxypropyl)carbamoyl]-5-fluorouracil

1-[N-(3-tert-Butoxycarbonylpropyl)carbamoyl]-5-fluorouracil (400 mg.) obtained in Example 31 was suspended in anisole (0.4 ml.). Trifluoroacetic acid (1.6 ml.) was added to the suspension under ice-cooling and stirred for 40 minutes at ambient temperature. The resultant solution was concentrated under reduced pressure to give residue, which was washed successively with ethanol, water, ethanol and diethylether to give the crystals of 1-[N-(3-carboxypropyl)carbamoyl]-5-fluorouracil (228 mg.).

M.p. 146°–147° C.

N.M.R. (DMSO-d$_6$): 1.73 (2H, quintet, J=7 Hz), 2.20 (2H, d, J=7 Hz), 3.30 (2H, quartet, J=7 Hz), 8.30 (1H, d, J=8 Hz), 9.07 (1H, t, J=6 Hz), 12.20 (1H, broad)

EXAMPLE 33

1-[N-(1-Adamantyl)carbamoyl]-5-fluorouracil

Diphenylphosphoryl azide (9.08 g.) was added dropwise to a solution of 1-admantanecarboxylic acid (5.4 g.) in dry pyridine (25 ml.) and stirred at 70° C. for one hour to give 1-adamantyl isocyanate [I.R.: 2250 cm$^{-1}$].

5-Fluorouracil (2.6 g.) was added to the solution and stirred at 100° C. for 7 hours. The resultant mixture was evaporated to dryness under reduced pressure. The residue was dissolved in ethyl acetate, chromatographed on silica gel, and eluted with ethyl acetate to give 1-[N-(1-adamantyl)carbamoyl]-5-fluorouracil (0.85 g.).

M.p. above 260° C.

N.M.R. (CDCl$_3$) (ppm): 1.5 to 2.3 (15H, m), 8.47 (1H, d, J=8 Hz), 9.0 (1H, broad s.), 9.47 (1H, broad s.)

EXAMPLE 34

1-[N-[2-(2-Norbornyl)ethyl]carbamoyl]-5-fluorouracil

Diphenylphosphoryl azide (6.05 g.) was added dropwise to a solution of 3-(2-norbornyl)propionic acid (3.36 g.) in dry pyridine (20 ml.) and stirred at 80° C. for 30 minutes to give 2-(2-norbornyl)ethyl isocyanate (I.R. 2260 cm$^{-1}$).

5-Fluorouracil (1.3 g.) was added to the solution and stirred at 100° C. for 4 hours. The resultant mixture was evaporated under reduced pressure. The residue was dissolved in ethyl acetate and washed with water. The ethyl acetate layer was dried over magnesium sulfate, filtered and concentrated. The residue was recrystallized from ethanol to give cristals of 1-[N-[2-(2-norbornyl)ethyl]carbamoyl]-5-fluorouracil (0.6 g.).

M.p. 128°–130° C.

N.M.R. (CDCl$_3$) (ppm): 0.9 to 2.6 (15H, m), 8.46 (1H, d, J=7 Hz), 9.0 (1H, d, J=7 Hz), 9.78 (1H, s)

EXAMPLE 35

D,L-1-[N-(3-Ethoxycarbonylnorborn-2-yl)carbamoyl]-5-fluorouracil

5-Norbornen-2,3-dicarboxylic anhydride was treated with ethanol to provide D,L-5-norbornene-2,3-dicarboxylic acid monoethyl ester substantially in the similar manner described for the preparation of D,L-5-norbornene-2,3-dicarboxylic acid monomethyl ester described in Example 23.

N.M.R. (CDCl$_3$) (ppm): 1.20 (3H, t, J=8 Hz), 1.40 (2H, quartet, J=8 Hz), 3.30 (2H, s), 4.04 (2H, quartet, J=8 Hz), 6.24 (2H, m), 16.32 (1H, s)

D,L-Norbornane-2,3-dicarboxylic acid monoethyl ester was prepared from D,L-5-norbornene-2,3-dicarboxylic acid monoethyl ester substantially in the similar manner to that of D,L-norbornane-2,3-dicarboxylic acid monomethyl ester described in Example 24.

N.M.R. (CDCl$_3$) (ppm): 1.10 to 1.93 (9H, m), 2.60 (2H, s), 3.00 (2H, s), 4.10 (2H, quartet, J=7 Hz), 10.83 (1H, s)

Diphenylphosphoryl azide (10.11 g.) was added dropwise to a solution of D,L-norbornane-2,3-dicarboxylic acid monoethyl ester (7.09 g.) in dry pyridine (25 ml.) and stirred at 80° C. for 35 minutes to give D,L-3-ethoxycarbonylnorborn-2-yl isocyanate (I.R.: 2280 cm$^{-1}$).

5-Fluorouracil (3.25 g.) was added to the solution and stirred at 80° C. for 4 hours. The resultant mixture was evaporated under reduced pressure. The residue was dissolved in ethyl acetate and washed with dilute hydrochloric acid and water. Ethyl acetate layer was dried over magnesium sulfate, filtered and evaporated to give residue, which was recrystallized from ethanol to give colorless crystals of D,L-1-[N-(3-ethoxycarbonylnorborn-2-yl)carbamoyl]-5-fluorouracil (2.91 g.).

M.p. 160°–161° C.

N.M.R. (DMSO-d$_6$) (ppm): 1.13 (3H, t, J=7 Hz), 1.48 (7H, broad s), 3.10 (2H, m), 4.06 (2H, quintet, J=7 Hz), 4.37 (1H, dd, J=8 Hz, J=8 Hz), 8.38 (1H, d, J=7 Hz), 10.0 (1H, d, J=8 Hz), 12.2 (1H, s)

EXAMPLE 36

D,L-1-[N-(3-Isopropoxycarbonylnorborn-2-yl)carbamoyl]-5-fluorouracil

5-Norbornene-2,3-dicarboxylic anhydride (20.0 g.) was added to a solution of sodium isopropoxide on isopropanol which was prepared from sodium (2.78 g.) and isopropanol (100 ml.). The solution was refluxed for 2 hours, and evaporated under reduced pressure. The residue was dissolved in water and overlapped with ethyl acetate. The mixture was adjusted to pH 1 with 10% hydrochloric acid under ice-cooling. The ethyl acetate layer was dried over magnesium sulfate, treated with activated charcoal, filtered, and concentrated to dryness to give crystalline powders of D,L-5-norbornene-2,3-dicarboxylic acid monopropyl ester (20.49 g.).

N.M.R. (DMSO-d$_6$) (ppm): 1.20 (6H, d, J=8 Hz), 1.43 (2H, m), 3.03 (2H, broad s), 3.13 to 3.20 (2H, s), 4.92 (1H, quintet, J=8 Hz), 6.17 (2H, m)

D,L-Norbornane-2,3-dicarboxylic acid monoisopropyl ester was obtained by catalytic reduction of D,L-5-norbornene-2,3-dicarboxylic acid monoisopropyl ester substantially in the similar manner to that of D,L-norbornane-2,3-dicarboxylic acid monomethyl ester described in Example 24.

N.M.R. (DMSO-d$_6$) (ppm): 1.13 to 1.80 (12H, m), 2.53 (3H, m), 2.97 (1H, quartet, J=5 Hz), 4.87 (1H, quintet, J=8 Hz)

Diphenylphosphoryl azide (13.48 g.) was added dropwise to a solution of D,L-norbornane-2,3-dicarboxylic acid monoisopropyl ester (11.08 g.) in dry pyridine (41 ml.) and stirred at 100° C. for one hour to give D,L-3-isopropoxycarbonylnorborn-2-yl isocyanate (I.R.: 2260 cm$^{-1}$).

5-Fluorouracil (5.31 g.) was added to the solution and stirred at 100° C. for 4 hours. The resultant mixture was evaporated under reduced pressure. The residue was dissolved in ethyl acetate and washed with dilute hydrochloric acid and water. Ethyl acetate layer was dried over magnesium sulfate, treated with activated charcoal, filtered and concentrated under reduced pressure. The residue obtained was recrystallized from ethanol to give D,L-1-[N-(3-isopropoxycarbonylnorborn-2-yl)-5-fluorouracil (275 mg.).

M.p. 135°–136° C.

N.M.R. (CDCl$_3$) (ppm): 1.23 (6H, d, J=8 Hz), 1.37 to 2.07 (7H, m), 2.50 (2H, broad s), 4.45 (1H, m), 5.03 (1H, q, J=8 Hz), 8.47 (1H, d, J=7 Hz), 10.97 (1H, d, J=7 Hz).

EXAMPLE 37

D,L-1-[N-(3-tert-Butoxycarbonyl-2-norbornyl)carbamoyl]-5-fluorouracil

Potassium tert-butoxide (50.0 g.) was dissolved in tert-butyl alcohol (200 ml.) under heating. To the solution was added portionwise 5-norbornene-2,3-dicarboxylic anhydride (58.53 g.). The mixture was refluxed and evaporated under reduced pressure. The residue was dissolved in aqueous sodium bicarbonate solution, overlapped with ethyl acetate and adjusted to pH 4.0 with 10% hydrochloric acid. The ethyl acetate layer was washed with water, dried over magnesium sulfate, treated with activated charcoal, filtered and concentrated under reduced pressure to give crystals D,L-3-tert-butoxycarbonyl-5-norbornene-2-carboxylic acid (72.80 g.).

N.M.R. (DMSO-d$_6$) (ppm): 1.45 (9H, s), 2.43 (2H, m), 3.05 (2H, m), 3.17 (1H, s), 3.20 (1H, s), 6.13 (1H, m), 6.40 (1H, m), 13.97 (1H, broad s)

D,L-3-tert-Butoxycarbonyl-norbornane-2-carboxylic acid was obtained by the catalytic reduction of D,L-3-tert-butoxycarbonyl-5-norbornene-2-carboxylic acid substantially in the similar manner to that of D,L-norbornane-2,3-dicarboxylic acid monomethyl ester described in Example 24.

N.M.R. (DMSO-d$_6$) (ppm): 1.13 to 1.77 (15H, m), 2.50 (3H, m), 2.97 (1H, m)

Diphenylphosphoryl azide (45.73 g.) was added dropwise to a solution of D,L-3-tert-butoxycarbonyl-norbornane-2-carboxylic acid (36.30 g.) in dry pyridine (126 ml.) and stirred at 100° C. for 40 minutes to give D,L-3-tert-butoxycarbonyl-2-norbornyl isocyanate (I.R.: 2270 cm$^{-1}$).

5-Fluorouracil (16.39 g.) was added to the above solution and stirred for 100° C. for 4 hours. The resultant mixture was treated substantially in the similar manner to that of D,L-1-[N-(3-ethoxycarbonyl-2-norbornyl)]-5-fluorouracil described in Example 35 to give D,L-1-[N-(3-tert-butoxycarbonyl-2-norbornyl)carbamoyl]-5-fluorouracil (10.35 g.).

M.p. 161° C.

N.M.R. (DMSO-d$_6$) (ppm): 1.40 (14H, m), 2.03 (1H, m), 2.40 (1H, m), 3.33 (2H, m), 4.28 (1H, m), 8.46 (1H, d, J=7 Hz), 11.13 (1H, d, J=7 Hz)

EXAMPLE 38

D,L-1-[N-(3-Carboxy-2norbornyl)carbamoyl]-5-fluorouracil

D,L-1-[N-(3-tert-butoxycarbonyl-2-norbornyl)carbamoyl]-5-fluorouracil (2.0 g.) prepared in Example 37 was suspended in anisole (2 ml.). Trifluoroacetic acid (8 ml.) was added to the suspension under ice-cooling and stirred for 30 minutes at ambient temperature. The resultant solution was concentrated under reduced pressure, added with diethyl ether and filtered. The filtrate was washed with diethyl ether and recrystallized with ethanol to give D,L-1-[N-(3-carboxy-2-norbornyl)carbamoyl]-5-fluorouracil.

M.p. 161° C.

N.M.R. (DMSO-d$_6$) (ppm): 1.17 to 1.67 (5H, m), 2.05 (1H, m), 2.43 (1H, m), 4.30 (1H, m), 8.47 (1H, d, J=8 Hz), 11.10 (1H, d, J=7 Hz), 14.10 (2H, broad)

EXAMPLE 39

D,L-1-[N-[3-(N,N-Diisopropylcarbamoyl)-2-norbornyl]carbamoyl]-5-fluorouracil

The mixture of 5-norbornene-2,3-dicarboxylic anhydride (20.0 g.) and diisopropylamine (70 ml.) was refluxed for 40 minutes and evaporated under reduced pressure to remove the excess diisopropylamine. The residue was dissolved in aqueous sodium bicarbonate solution and then to aqueous potassium carbonate solution. The alkaline solution was acidified with 10% hydrochloric acid to pH 1.5 under ice-cooling to give the precipitates, which were filtered, washed with water and dried over phosphoric pentaoxide to give crystalline D,L-3-(N,N-diisopropylcarbamoyl)-5-norbornene-2-carboxylic acid (26.67 g.).

N.M.R. (DMSO-d$_6$) (ppm): 1.00 to 1.32 (14H, m), 2.90 to 3.00 (2H, broad doublet), 3.28 (2H, s), 3.33 (1H, quintet, J=7 Hz), 4.06 (1H, quintet, J=7 Hz), 5.95 (1H, m), 6.27 (1H, m)

D,L-3-(N,N-diisopropylcarbamoyl)-2-norbornanecarboxylic acid was prepared from D,L-3-(N,N-diisopropylcarbamoyl)-5-norbornene-2-carboxylic acid substantially in the similar manner to that of D,L-norbornane-2,3-dicarboxylic acid monomethyl ester described in Example 24.

N.M.R. (DMSO-d$_6$) (ppm): 1.05 to 1.33 (16H, m), 1.77 (2H, m), 2.33 (2H, broad s), 2.73 (1H, d), 3.27 (2H, m), 4.00 (1H, quintet, J=6 Hz).

Diphenylphosphoryl azide (11.32 g.) was added dropwise to a solution of D,L-3-(N,N-diisopropylcarbamoyl)-2-norbornanecarboxylic acid (10.0 g.) in dry pyridine (32 ml.) and stirred at 80° C. for 35 minutes to give D,L-3-(N,N-diisopropylcarbamoyl)-2-norbornylisocyanate (I.R.: 2270 cm$^{-1}$).

5-Fluorouracil (4.05 g.) was added to the solution and stirred at 80° C. for 3 hours. The resultant mixture was evaporated under reduced pressure. The residue was dissolved in ethyl acetate. The precipitates partially formed during washing with dilute hydrochloric acid were filtered and washed with ethanol and diethyl ether. The ethyl acetate layer was washed with water, dried over magnesium sulfate, treated with activated charcoal, filtered and evaporated under reduced pressure to give crystals. The residue and the precipitates obtained above were combined and recrystallized from ethanol to give crystals of D,L-1-[N-[3-(N,N-diisopropylcarbamoyl)-2-norbornyl]carbamoyl]-5-fluorouracil (754 mg.).

M.p. 201°–202° C.

N.M.R. (DMSO-$d_6$) (ppm): 1.06 to 1.71 (20H, m), 2.47 (2H, m), 3.20 to 3.63 (2H, m), 4.07 to 4.47 (2H, m), 8.60 (1H, d, J=8 Hz), 12.67 (1H, d, J=8 Hz), 14.17 (1H, broad s)

EXAMPLE 40

D,L-1-[N-(3-Ethoxycarbonyl-5-norbornen-2-yl)carbamoyl]-5-fluorouracil

Diphenylphosphoryl azide (14.4 g.) was added dropwise to a solution to D,L-5-norbornene-2,3-dicarboxylic acid monoethyl ester (10.0 g.) in dry pyridine (40 ml.) and stirred at 80° C. for 50 minutes to give 3-ethoxycarbonyl-5-norbornen-2-yl isocyanate (I.R.: 2260 cm$^{-1}$).

5-Fluorouracil (6.19 g.) was added to the solution and stirred at 80° C. for 2 hours. The resultant mixture was evaporated under reduced pressure. The residue was dissolved in ethyl acetate and washed with dilute hydrochloric acid and water. The ethyl acetate layer was dried over magnesium sulfate, treated with activated charcoal, filtered and evaporated. The residue was washed with isopropyl ether, triturated with ethanol and crystallized from ethanol to give D,L-1-[N-(3-ethoxycarbonyl-5-norbornen-2-yl)carbamoyl]-5-fluorouracil (1.67 g.)

M.p. 150°–152° C.

N.M.R. (DMSO-$d_6$) (ppm): 1.08 (3H, t, J=7 Hz), 1.46 (2H, m), 3.08 (2H, broad s), 3.36 (1H, dd, J=8 Hz, J=3 Hz), 3.96 (2H, quintet, J=7 Hz), 4.80 (1H, double triplet, J=8 Hz, J=3 Hz), 6.12 (1H, m), 6.48 (1H, m), 8.40 (1H, d, J=7 Hz), 9.08 (1H, d, J=8 Hz)

EXAMPLE 41

D,L-1-[N-(3-tert-Butoxycarbonyl-5-norbornen-2-yl)carbamoyl]-5-fluorouracil

Diphenylphosphoryl azide (37.47 g.) was added dropwise to a solution of D,L-3-tert-butoxycarbonyl-5-norbornene-2-carboxylic acid (32.46 g.) prepared in Example 37 in dry pyridine (115 ml.) and stirred at 100° C. for 40 minutes to give 3-tert-butoxycarbonyl-5-norbornen-2-yl isocyanate (I.R.: 2260 cm$^{-1}$).

5-Fluorouracil (14.74 g.) was added to the solution and stirred at 100° C. for 4 hours. The resultant mixture was evaporated under reduced pressure. The residue was dissolved in ethyl acetate and washed with dilute hydrochloric acid and water, dried over magnesium sulfate, treated with activated charcoal, filtered and concentrated under reduced pressure. The residue was washed with petroleum ether and triturated with diethyl ether. The precipitates were crystallized from ethanol to give D,L-1-[N-(3-tert-butoxycarbonyl-5-norbornen-2-yl)carbamoyl]-5-fluorouracil (1.55 g.).

M.p. 146° C.

N.M.R. (DMSO-$d_6$) (ppm): 1.4 to 1.93 (11H, m), 3.00 (2H, broad s), 3.27 (1H, s), 4.53 (1H, quintet, J=4 Hz), 6.17 (1H, m), 6.50 (1H, m), 8.33 (1H, d, J=7 Hz), 8.93 (1H, d, J=8 Hz), 12.20 (1H, broad s)

EXAMPLE 42

D,L-1-[N-(3-carboxy-5-norbornen-2-yl)-carbamoyl]-5-fluorouracil

D,L-1-[N-(3-carboxy-5-norbornen-2-yl)carbamoyl]-5-fluorouracil was prepared from D,L-1-[N-(3-tert-butoxycarbonyl-5-norbornen-2-yl)carbamoyl]-5-fluorouracil prepared in Example 41 substantially in the similar manner to that of 1-[N-(3-carboxypropyl)carbamoyl]-5-fluorouracil described in Example 32.

M.p. 169° C.

N.M.R. (DMSO-$d_6$) (ppm): 1.33 to 1.97 (3H, m), 3.03 (2H, s), 4.57 (1H, quintet, J=4 Hz), 6.13 (1H, m), 6.50 (1H, m), 8.33 (1H, d, J=7 Hz), 8.93 (1H, d, J=8 Hz), 12.20 (1H, d, J=4 Hz)

EXAMPLE 43

1-[N-[2-(5-Norbornen-2-yl)ethenyl]carbamoyl]-5-fluorouracil

Diphenylphosphoryl azide (12.1 g.) was added dropwise to a solution of 3-(5-norbornen-2-yl)acrylic acid (6.57 g.) in dry pyridine (30 ml.) and stirred at 80° C. for 30 minutes to give 2-(5-norbornen-2-yl)ethenyl isocyanate (I.R.: 2260 cm$^{-1}$).

5-Fluorouracil (2.6 g.) was added to the solution and stirred at 100° C. for 4 hours. The resultant mixture was evaporated under reduced pressure. The residue was dissolved in ethyl acetate and washed with water. The ethyl acetate layer was dried over magnesium sulfate, filtered and evaporated under reduced pressure. The residue was crystallized from ethanol to give 1-[N-[2-(5-norbornen-2-yl)ethenyl]carbamoyl]-5-fluorouracil (0.3 g.).

M.p. 130°–132° C.

N.M.R. (DMSO-$d_6$) (ppm): 1.0 to 2.9 (7H, m), 5.5 to 6.3 (4H, m), 7.71 [nh]*$^{(a)}$, 9.30 [h]*$^{(b)}$ (1H, d, J=6 Hz; d, J=8 Hz), 8.35 (1H, d, J=7 Hz)

(*a) [nh]; non-hydrogen-bonded
(*b) [h]; hydrogen-bonded

EXAMPLE 44

D,L-1-[N-(3-Isopropoxycarbonyl-5-norbornen-2-yl)carbamoyl]-5-fluorouracil

Diphenylphosphoryl azide (24.5 g.) was added dropwise to a solution of D,L-5-norbornene-2,3-dicarboxylic acid monoisopropyl ester (20.0 g.) prepared in Example 36 in dry pyridine (100 ml.) and stirred for 40 minutes at 100° C. to give a solution of D,L-3-isopropoxycarbonyl-5-norbornen-2-yl isocyanate [I.R.: 2260 cm$^{-1}$].

5-Fluorouracil (12.8 g.) was added to the solution of D,L-3-isopropoxycarbonyl-5-norbornen-2-yl isocyanate and stirred at 100° C. for 2 hours. The resultant mixture was evaporated to dryness under reduced pressure. The residue was dissolved in ethyl acetate, washed with dilute hydrochloric acid and water, dried over magnesium sulfate, treated with activated charcoal, filtered and concentrated to dryness under reduced pressure. The residue was dissolved in ethyl acetate, chromatographed on silica gel, and eluted with ethyl acetate to give crystalline powders. Recrystallization from ethanol gave colorless crystals of D,L-1-[N-(3-isopropoxycarbonyl-5-norbornen-2-yl)carbamoyl]-5-fluorouracil (375 mg.).

M.p. 148° C.

N.M.R. (DMSO-d$_6$) (ppm): 1.00 (3H,d,J=7 Hz), 1.13 (3H,d,J=7 Hz), 1.43 (2H,broad,s.), 3.07 to 3.43 (3H,m), 4.57 to 4.97 (2H, m), 6.13 (1H,m), 6.47 (1H,m), 8.40 (1H,d,J=7 Hz), 9.07 (1H,d,J=9 Hz), 12.27 (1H, broad).

EXAMPLE 45

D,L-1-[N-(3-Ethoxycarbonyl-5,6-isopropylidenedioxy-2-norbornyl)carbamoyl]-5-fluorouracil D,L-5-Norbornene-2,3-dicarboxylic acid monoethyl ester (18.0 g.) was dissolved in a solution of potassium hydroxide (12.0 g.) in water (130 ml.) at −3° C. Potassium permanganate (14.9 g.) was portionwise added to the solution during 25 minutes below −3° C. To the solution was added a mixture of sulfur dioxide (12 g.) and 50% sulfuric acid (40 g.). The mixture was heated to the boiling point, cooled to the room temperature. After filtration of the precipitates formed, the filtrate was overlayed with ethyl acetate, adjusted with 10% hydrochloric acid to pH 1. The ethyl acetate layer was dried over magnesium sulfate, treated with activated charcoal, filtered and then concentrated to dryness under reduced pressure to give oily D,L-5,6-dihydroxynorbornane-2,3-dicarboxylic acid monoethyl ester (11.2 g.).

N.M.R. (D$_2$O) (ppm): 1.23 (3H,t,J=7 Hz), 1.37 (1H, m), 1.90 (1H,m), 2.50 (2H,m), 3.17 ((2H,m), 4.10 (2H, quintet, J=7 Hz).

A solution of D,L-5,6-dihydroxynorbornane-2,3-dicarboxylic acid monoethyl ester (11.2 g.), 2,2-dimethoxypropane (4.78 g.) and p-toluenesulfonic acid (5 mg.) in dry N,N-dimethylformamide was refluxed for 2 hours under reduced pressure at 60°-65° C. The resultant mixture was evaporated under reduced pressure. The residue was dissolved in aqueous sodium bicarbonate solution under ice-cooling, washed with ethyl acetate, treated with activated charcoal and then filtered. The solution was overlayed with ethyl acetate, adjusted to pH 3.5 with 10% hydrochloric acid under ice-cooling. The ethyl acetate layer was washed with saturated aqueous sodium chloride solution, dried over magnesium sulfate, treated with activated charcoal, filtered and concentrated to dryness under reduced pressure to give oily D,L-5,6-isopropylidenedioxynorbornane-2,3-dicarboxylic acid monoethyl ester (9.29 g.).

N.M.R. (CDCl$_3$) (ppm): 1.10 to 1.43 (10H, m), 1.87 (1H,broad s), 2.60 (2H, broad s), 3.07 ((2H,m), 4.10 (2H, quintet, J=7 Hz), 4.57 (2H,m).

Diphenylphosphoryl azide (6.85 g.) was added to a solution of D,L-5,6-isopropylidenedioxynorbornane-2,3-dicarboxylic acid monoethyl ester in dry pyridine (22 ml.). The solution was stirred for 45 minutes at 90° C. to give a solution comprising D,L-5,6-isopropylidenedioxy-3-ethoxycarbonyl-2-norbornyl isocyanate [I.R.; 2270 cm$^{-1}$].

5-Fluorouracil (2.71 g.) was added to the solution of D,L-5,6-isopropylidenedioxy-3-ethoxycarbonyl-2-norbornyl isocyanate and stirred at 90° C. for 2 hours. The resultant solution was evaporated under reduced pressure. The residue was dissolved in ethyl acetate, washed with dilute hydrochloric acid and water, dried over magnesium sulfate, treated with activated charcoal, filtered and evaporated under reduced pressure. The residue was triturated with petroleum ether, to which ethanol was added, and filtered. The obtained powders were recrystallized from ethanol to give crystalline 1-[N-(3-ethoxycarbonyl-5,6-isopropylidenedioxy-2-norbornyl)carbamoyl]-5-fluorouracil (1.50 g.).

M.p. 173°-175° C.

N.M.R. (CDCl$_3$) (ppm): 1.13 to 1.43 (10H, m), 1.80 to 2.00 (1H, m), 2.73 (2H, broad s), 3.10 (double doublet, J=11 Hz, J=5 Hz), 4.00 to 4.60 (5H, m), 8.47 (1H, d, J=7 Hz), 9.33 (1H, broad s), 10.10 (1H, d, J=8 Hz).

EXAMPLE 46

1-[N-(3-Methyladamantan-1-ylmethyl)carbamoyl]-5-fluorouracil

Diphenylphosphoryl azide (6.41 g.) was added dropwise to a solution of 3-methyladamantan-1-ylacetic acid (4.85 g.) in dry pyridine (20 ml.) and stirred at 100° C. for 40 minutes to give 3-methyladamantan-1-ylmethyl isocyanate [I.R.: 2260 cm$^{-1}$]. 5-Fluorouracil (2.52 g.) was added to the solution and stirred at 100° C. for 2 hours. The resultant mixture was evaporated under reduced pressure. The residue was dissolved in ethyl acetate and washed with dilute hydrochloric acid and water. Ethyl acetate layer was dried over magnesium sulfate, filtered and evaporated to give residue, which was recrystallized from ethanol to give colorless crystals of 1-[N-(3-methyladamantan-1-ylmethyl)carbamoyl]-5-fluorouracil. (984 mg.)

M.p. 172° C.

N.M.R. (DMSO-d$_6$) (ppm): 0.77 (3H, s), 1.20 to 1.53 (12H, m), 2.00 (2H, broad s), 3.00 (2H, d, J=6 Hz), 8.33 (1H, d, J=8 Hz), 9.13 (1H, t, J=6 Hz), 12.27 (1H, broad).

EXAMPLE 47

(+)-1-[N-(3-Pinanyl)carbamoyl]-5-fluorouracil

The reaction of (+)-pinane-3-carboxylic acid and diphenyl phosphoryl azide in dry pyridine provided a solution comprising (+)-3-pinanyl isocyanate [I.R.: 2260 cm$^{-1}$], which was reacted with 5-fluorouracil to provide (+)-1-[N-(3-pynanyl)carbamoyl]-5-fluorouracil substantially in the similar method to that of Example 45.

M.p. 189° C.

N.M.R. (DMSO-d$_6$) (ppm): 1.00 to 1.24 (9H, m), 1.56 to 2.04 (5H, m), 2.32 to 2.64 (2H, m), 4.12 (1H, m), 8.36 (1H, d, J=8 Hz), 9.12 (1H, d, J=10 Hz).

EXAMPLE 48

1-[N-(3-Bromoadamantan-1-ylmethyl)carbamoyl]-5-fluorouracil

The reaction of 3-bromoadamantan-1-ylacetic acid and diphenyl phosphoryl azide in dry pyridine provided a solution comprising 3-bromoadamantan-1-ylmethyl isocyanate [I.R.: 2270 cm$^{-1}$], which was reacted with 5-fluorouracil to provide 1-[N-(3-bromoadamantan-1-ylmethyl)carbamoyl]-5-fluorouracil substantially by the similar method to that of Example 45.

M.p. 185°-186° C.

N.M.R. (DMSO-d$_6$) (ppm): 1.53 to 1.66 (6H, m), 2.13 (2H, s), 2.27 (6H, s), 3.12 (2H, d, J=6 Hz), 8.43 (1H, d, J=8 Hz), 9.20 (1H, t, J=6 Hz), 12.37 (1H, broad).

EXAMPLE 49

D,L-1-[N-(3-Ethoxycarbonylbicyclo[2.2.2]-oct-2-yl)carbamoyl]-5-fluorouracil

Sodium (1.29 g.) was dissolved in ethanol (80 ml.) under heating. To the solution was added portionwise D,L-bicyclo[2.2.2]-oct-2-ene-5,6-dicarboxylic anhydride (10.0 g.). The mixture was refluxed for 7 hours and evaporated under reduced pressure. The residue was dissolved in aqueous sodium bicarbonate solution, overlapped with ethyl acetate and adjusted to pH 3.0 with 10% hydrochloric acid. The ethyl acetate layer was washed with water, dried over magnesium sulfate, treated with activated charcoal, filtered and concentrated under reduced pressure to give crystals of D,L-6-ethoxycarbonylbicyclo[2.2.2]oct-2-en-5-carboxylic acid (12.61 g.).

N.M.R. (DMSO-$d_6$) (ppm): 1.12 (5H, m), 1.56 (2H, m), 2.76 (2H, broad s), 2.96 (2H, s), 3.92 (2H, quintet, J=6 Hz), 6.16 (2H, m).

D,L-6-ethoxycarbonylbicyclo[2.2.2]oct-2-ene-5-carboxylic acid (3.00 g.) which was prepared above was dissolved in tetrahydrofuran (30 ml.), and hydrogenated over 10% palladium charcoal catalyst under hydrogen atmosphere of ordinary pressure at ambient temperature. The reaction mixture was filtrated and the filtrate was concentrated in vacuo. The oily residue was made solidified and dried to give D,L-3-ethoxycarbonylbicyclo[2.2.2]octane-2-carboxylic acid (2.86 g.).

N.M.R. (DMSO-$d_6$) (ppm): 1.03 to 1.87 (13H, m), 2.87 (2H, s), 3.97 (2H, quintet, J=6 Hz).

The reaction of 3-ethoxycarbonylbicyclo[2.2.2]-octane-2-carboxylic acid prepared above and diphenyl phosphoryl azide in dry pyridine provided a solution comprising 3-ethoxycarbonylbicyclo[2.2.2]oct-2-yl isocyanate [I.R.: 2270 cm$^{-1}$], which was reacted with 5-fluorouracil to provide D,L-1-[N-(3-ethoxycarbonylbicyclo[2.2.2]oct-2-yl)carbamoyl]-5-fluorouracil (1.5 g.) substantially in the similar method to that of Example 45.

M.p. 145°-155° (dec.).

N.M.R. (DMSO-$d_6$) (ppm): 1.10 (3H, s), 1.35 to 1.92 (10H, m), 3.98 (1H, d, J=10 Hz), 4.00 (2H, quartet, J=7 Hz), 4.33 (1H, m), 8.33 (1H, d, J=7 Hz), 9.75 (1H, d, J=8 Hz), 10.40 (1H, broad s).

EXAMPLE 50

1-[N-(2-Adamantylmethyl)carbamoyl]-5-fluorouracil

The reaction of 2-adamantylacetic acid and diphenyl phosphoryl azide in dry pyridine provided a solution comprising 2-adamantylmethyl isocyanate [I.R.: 2260 cm$^{-1}$], which was reacted with 5-fluorouracil to provide 1-[N-(2-adamantylmethyl)carbamoyl]-5-floururacil substantially in the similar method to that of Example 45.

M.p. 274°-278° C.

N.M.R. (DMSO-$d_6$) (ppm): 1.4 to 1.9 (15H, m), 3.38 (2H, dd, J=7 Hz, J=8 Hz), 9.38 (1H, d, J=8 Hz), 9.78 (1H, t, J=6 Hz).

EXAMPLE 51

D,L-1-[N-(2-Methoxycarbonylnorborn-3-yl)carbamoyl]-5-fluorouracil

A solution of ethyl chlorocarbonate (60.8 g.) in tetrahydrofuran (50 ml.) was added dropwise to a solution of D,L-norbornan-2,3-dicarboxylic acid monomethyl ester (100 g.) which was prepared by the method described in Example 24 and trimethylamine (51.6 g.) with stirring at −10° C., liberating triethylamine hydrochloride as a milky precipitate. The mixture was further stirred for one hour at the same temperature. A solution of sodium azide (36.5 g.) in water (200 ml.) was added to the mixture. The clear solution was further stirred for one hour at 0° C., liberating another milky precipitate, and then evaporated in vacuo to remove tetrahydrofuran. To the residue was added water (1000 ml.) to dissolve the mily precipitate. The mixture was extracted with ethy acetate (1000 ml×2). The ethyl acetate layer was separated and washed with water, dried over magnesium sulfate and filtered.

The filtrate was stirred for two hours at 55° C., and evaporated in vacuo to give oily residue (93.6 g.). The residue was distilled under reduced pressure to give a colorless liquid of D,L-2-methoxycarbonylnorborn-3-yl isocyanate (70.6 g.). B.p. 90°-100° C./0.2 mm Hg.

I.R. (Nujol): 1270 cm$^{-1}$.

A solution of 5-fluorouracil (26.7 g.) and D,L-2-methoxycarbonylnorborn-3-yl isocyanate (58.7 g.) in pyridine (110 ml.) was heated with stirring for 1 hour at 90° C. and evaporated in vacuo. The residue was triturated with isopropyl ether (100 ml×2) and water (100 ml×3). The substance was filtered, dried and recrystalized with ethanol to give D,L-1-[N-(2-methoxycarbonylnorborn-3-yl)carbamoyl]-5-fluorouracil (53.5 g.).

M.p. 164°-165° C.

N.M.R. (DMSO-$d_6$) (ppm): 1.5 (6H, broad s), 2.33 to 2.67 (2H), 2.9 to 3.4 (1H, m), 3.6 (3H, s), 4.07 to 4.6 (1H, m), 8.4 (1H, d, J=8 Hz), 10.07 (1H, d, J=8 Hz), 12.3 (1H, broad s).

EXAMPLE 52

D,L-1-[N-[3-(N-tert-Butoxycarbonylamino)norborn-2-yl]carbamoyl]-5-fluorouracil

A solution of D,L-2-methoxycarbonylnorborn-3-yl isocyanate (1.16 g.) prepared by the method described in Example 51 in ethanol (10 ml.) was heated under reflux for 3 hours, and evaporated in vacuo to give methyl D,L-3-ethoxycarbonylaminonorbornane-2-carboxylate (1.37 g.) as a oily residue.

I.R. (Nujol): 3400, 1715 cm$^{-1}$.

Methyl D,L-3-ethoxycarbonylaminonorbornan-2-carboxylate (1.34 g.) in 40% aqueous sodium hydroxide solution (5 ml.) was heated under reflux with stirring for 1 hour, liberating precipitate. The precipitate was filtered and dissolved in a small amount of water. The solution was adjusted to pH 3.5 with concentrated hydrochloric acid, liberating precipitate. The precipitate was filtered, washed with water and dried over phosphorus pentoxide to give 3-aminonorbornane-2-carboxylic acid (0.8 g.).

I.R. (Nujol): 1620-1560 cm$^{-1}$.

To a solution of 3-aminonorbornane-2-carboxylic acid (12.6 g.) in a mixture of water (100 ml.) and dioxane (100 ml.) were added triethylamine (12.2 g.) and 2-tert-butoxycarbonyloxyimino-2-phenylacetonitrile (16.2 g.). The mixture was stirred for 5 hours at ambient temperature and washed with ethyl acetate at pH 10 (each 250 ml., 2 times). The aqueous layer was adjusted to pH 2 with 10% aqueous hydrochloric acid. The acidified solution was extracted with ethyl acetate. The organic layer was dried over magnesium sulfate and filtered. The filtrate was evaporated to dryness under reduced pressure. The residue was pulverized with isopropyl ether to give 3-(N-tert-butoxycarbonylamino)norbornane-2-carboxylic acid (10.5 g.).

I.R. (Nujol): 3250, 2600-2500, 1710, 1690, 1650 cm$^{-1}$

N.M.R. (CDCl$_3$) (ppm): 1.25-1.75 (15H, m), 2.43 (1H, broad s), 2.66 (1H, broad s), 3.93 (1H, m).

The reaction of 3-(N-tert-butoxycarbonylamino)norbornane-2-carboxylic acid (2 g.) and diphenylphosphoryl azide in pyridine provided a solution comprising D,L-N-[3-(N-tert-butoxycarbonylamino)norborn-2- yl]carbamoyl isocyanate, which was reacted with 5-fluorouracil to provide D,L-1-[N-[3-(N-tert-butoxycarbonylamino)norborn-2-yl]carbamoyl]-5-fluorouracil substantially in the similar method to that of Example 33.

I.R. (Nujol): 3300–3250, 1730, 1705, 1670 cm$^{-1}$.
N.M.R. (DMSO-d$_6$) (ppm): 1.0–1.5 (15H, m), 2.20 (1H, broad s), 2.62 (1H, broad s), 3.70 (2H, m), 8.27 (1H, d, J=8 Hz), 9.23 (1H, d, J=8 Hz).

EXAMPLE 53

D,L-1-[N-(3-Amino-2-norbornyl)carbamoyl]-5-fluorouracil

D,L-1-[N-[3-(N-tert-Butoxycarbonylamino)norborn-2-yl]carbamoyl]-5-fluorouracil (2.5 g.) was dissolved in a mixture of methanol (30 ml.) and tetrahydrofuran (10 ml.).

Dry hydrogen chloride gas was passed into the above solution. The reaction mixture was evaporated to dryness at 35° C. in vacuo. The residue was washed with diethyl ether and pulverized in a mixture of methanol and diethylether to give D,L-1-[N-(3-amino-2-norbornyl)carbamoyl]-5-fluorouracil (0.85 g.).

I.R. (Nujol): 3250–3150, 1730, 1690, 1660 cm$^{-1}$
N.M.R. (DMSO-d$_6$) (ppm): 1.50 (8H, m), 3.50 (2H, m), 8.43 (1H, d, J=8 Hz), 8.70 (2H, broad s), 9.25 (1H, d, J=8 Hz), 13.93 (1H, broad s).

EXAMPLE 54

1-[N-(2-norbornen-6-yl)carbamoyl]-5-fluorouracil

A solution of ethyl chlorocarbonate (10 g.) in tetrahydrofuran (50 ml.) was added dropwise with stirring to a solution of 2-norbornene-6-carboxylic acid (12 g.) and triethylamine (10 g.) in tetrahydrofuran (110 ml.) at 0° C.

The solution was stirred at 0° C. for 3 hours.

A solution of sodium azide (7 g.) in water (50 ml.) was added to the solution at −20° C.

The solution was stirred at 0° C. for two hours and then concentrated in vacuo to a volume of 50 ml. at 35° C.

The solution was diluted with water (200 ml.), extracted with ethyl acetate. The organic layer was washed with water and then dried over magnesium sulfate.

After filtration, the filtrate was warmed with stirring to 70° C. for 2 hours and then evaporated in vacuo to dryness at 40° C. to give a solution comprising 2-norbornen-6-yl isocyanate (IR: 2270 cm$^{-1}$).

To the above solution of 2-norbornen-6-yl isocyante was added a solution of 5-fluorouracil (6 g.) in pyridine (70 ml.) at 90° C. and stirred for 2 hours.

The solution was evaporated in vacuo to dryness at 60° C. The residue was added with water (200 ml.) and then extracted with ethyl acetate. The organic layer was washed successively with aqueous diluted hydrochloric acid and water (3 times), dried over magnesium sulfate, evaporated in vacuo to dryness to give 1-[N-(2-norbornen-6-yl)carbamoyl]-5-fluorouracil (7.0 g.).

m.p. 180° C. (recrystallized from ethanol)
I.R. (Nujol): 3250, 1720 to 1740, 1680, 1665 cm$^{-1}$.
N.M.R. (DMSO-d$_6$) (ppm): 1.50 (6H, m), 2.83 (2H, s), 3.58 to 4.30 (1H, m), 5.95 to 6.30 (2H, m), 8.33 (1H, d, J=7 Hz), 9.16 (1H, d, J=7 Hz), 12.16 (1H, broad s).

EXAMPLE 55

D,L-1-[N-(6-ethoxycarbonylbicyclo[2.2.2]oct-2-en-5-yl)carbamoyl]-5-fluorouracil

A solution of ethyl chlorocarbonate (5.3 g.) in tetrahydrofuran (30 ml.) was added dropwise with stirring at 0° C. to a solution of D,L-6-ethoxycarbonylbicyclo[2.2.2]oct-2-ene-5-carboxylic acid which was prepared by the method described in Example 49 and triethylamine (5 g.) in tetrahydrofuran (90 ml.).

The solution was stirred at 0° C. for 2 hours. A solution of sodium azide (3.2 g.) in water (30 ml.) was added to the solution at −20° C. The solution was stirred at 0° C. for 2 hours and then concentrated in vacuo to a volume of 50 ml. at 35° C. The solution was diluted with water (200 ml.), extracted with ethyl acetate. The organic layer was washed with water and then dried over magnesium sulfate. After filtration, the filtrate was stirred at 70° C. for 2 hours to give a solution comprising D,L-6-ethoxycarbonylbicyclo[2.2.2]oct-2-en-5-yl isocyanate (I.R.: 2270 cm$^{-1}$).

To the above solution of D,L-6-ethoxycarbonylbicyclo[2.2.2]oct-2-en-5-yl isocyanate was added a solution of 5-fluorouracil (3.5 g.) in pyridine (60 ml.) at 90° C. with stirring for 2 hours.

The solution was evaporated to dryness in vacuo at 60° C., added with water (150 ml.) and extracted with ethyl acetate. The organic layer was washed successively with aqueous diluted hydrochloric acid and water (3 times), dried over magnesium sulfate and evaporated in vacuo to dryness to give D,L-1-[N-(6-ethoxycarbonylbicyclo[2.2.2]oct-2-en-5-yl)carbamoyl]-5-fluorouracil (2.1 g.).

m.p. 158°–162° C. (recrystallized from ethanol).
I.R. (Nujol): 3300, 1750, 1720, 1670, 1615 cm$^{-1}$
N.M.R. (DMSO-d$_6$) (ppm): 1.0 to 1.65 (7H, m), 2.0 (2H, m), 2.80 (2H, broad s), 4.0 to 4.4 (4H, m), 6.2 to 6.7 (1H, m), 8.30 (1H, d, J=7 Hz), 9.00 (1H, d, J=7 Hz), 12.40 (1H, broad s).

EXAMPLE 56

D,L-1-[N-(6-methoxycarbonylbicyclo[2.2.2]oct-2-en-5-yl)carbamoyl]-5-fluorouracil A solution of bicyclo[2.2.2]oct-2-ene-5,6-dicarboxylic acid anhydride (10 g.) in methanol (150 ml.) was refluxed for 4 hours with stirring. The solution was evaporated in vacuo to dryness to give D,L-6-methoxycarbonylbicyclo[2.2.2]oct-2-ene-5-carboxylic acid (10 g.) as white crystals.

m.p. 55°–58° C.
I.R. (Nujol): 1720, 1700, 1620 cm$^{-1}$.
N.M.R. (CDCl$_3$) (ppm): 1.50 (4H, m), 3.16 (4H, m), 3.60 (3H, s), 6.33 (2H, m).

A solution of ethyl chlorocarbonate (6 g.) in tetrahydrofuran (30 ml.) was added dropwise with stirring at 0° C. to a solution of D,L-methoxycarbonylbicyclo[2.2.2]oct-2-ene-5-carboxylic acid (10 g.) prepared above and triethylamine (5.6 g.) in tetrahydrofuran (90 ml.). The solution was stirred at 0° C. for 2 hours.

A solution of sodium azide (4 g.) in water (30 ml.) was added to the solution at −20° C. The solution was stirred at 0° C. for 2 hours and then concentrated in vacuo to a volume of 50 ml. at 35° C.

The solution was diluted with water (200 ml.), extracted with ethyl acetate.

The organic layer was washed with water and then dried over magnesium sulfate.

After filtration, the filtrate was stirred at 70° C. for 2 hours to give a solution comprising D,L-6-methoxycarbonylbicyclo[2.2.2]oct-2-en-5-yl isoyanate (I.R. 2270 cm$^{-1}$).

To the above solution of D,L-6-methoxycarbonylbicyclo[2.2.2]oct-2-en-5-yl isocyanate was added a solution of 5-fluorouracil (6 g.) in pyridine (70 ml.) at 90° C. with stirring for 2 hours. The solution was evaporated to dryness in vacuo at 60° C., added with water (200 ml.) and extracted with ethyl acetate. The organic layer was washed successively with aqueous diluted hydrochloric acid and water (3 times), dried over magnesium sulfate and evaporated in vacuo to dryness to give D,L-1-[N-(6-methoxycarbonylbicyclo[2.2.2]oct-2-en-5-yl)carbamoyl]-5-fluorouracil (5 g.).

m.p. 265°-267° C. (recrystallized from ethanol).

I.R. (Nujol): 3270, 3150, 1780-1740, 1685, 1660 cm$^{-1}$.

N.M.R. (DMSO-d$_6$) (ppm): 1.2 to 1.7 (4H, m), 2.7 to 3.2 (3H, m), 3.50 (3H, s), 4.3 to 4.7 (1H, m), 6.0 to 6.7 (2H, m), 8.30 (1H, d, J=8 Hz), 9.07 (1H, d, J=8 Hz), 12.27 (1H, broad s).

What we claim is:

1. A compound of the formula:

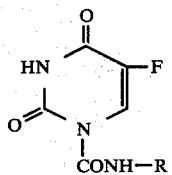

wherein R is a bridged alicyclic group selected from the group consisting of norbornyl, norbornenyl, bicyclo[2,2,2]-octyl, bicyclo[2,2,2]-2-octenyl, bicyclo[3,1,1]-heptyl and adamantyl optionally substituted by at least one substituent selected from the group consisting of lower alkyl, carboxy, lower alkoxycarbonyl, alkylidenedioxy, N,N-di(lower)-alkylcarbamoyl, amino, lower alkoxycarbonylamino and halogen.

2. The compound of claim 1, wherein R is said unsubstituted bridged alicyclic group.

3. The compound of claim 2, wherein R is norbornyl.

4. The compound of claim 3, wherein R is 2-norbornyl.

5. The compound of claim 2, wherein R is adamantyl.

6. The compound of claim 5, wherein R is 1-adamantyl.

7. The compound of claim 1, wherein said bridged alicyclic group is substituted by at least one of said substituents.

8. The compound of claim 7, wherein R is carboxynorbornyl.

9. The compound of claim 8, wherein R is 3-carboxy-2-norbornyl.

10. The compound of claim 8, wherein R is (lower)alkoxycarbonylnorbornyl.

11. The compound of claim 10, wherein R is methoxycarbonylnorbornyl.

12. The compound of claim 11, wherein R is 3-methoxycarbonyl-2-norbornyl.

13. The compound of claim 10, wherein R is ethoxycarbonylnorbornyl.

14. The compound of claim 13, wherein R is 3-ethoxycarbonyl-2-norbornyl.

15. The compound of claim 10, wherein R is isopropoxycarbonylnorbornyl.

16. The compound of claim 15, wherein R is 3-isopropoxycarbonyl-2-norbornyl.

17. The compound of claim 10, wherein R is 3-tert-butoxycarbonyl-2-norbornyl.

18. The compound of claim 7, wherein R is norbornyl which is substituted by (lower) alkoxycarbonyl and alkylidenedioxy.

19. The compound of claim 18, wherein R is norbornyl substituted by ethoxycarbonyl and isopropylidenedioxy.

20. The compound of claim 19, wherein R is 3-ethoxycarbonyl-5,6-isopropylidenedioxy-2-norbornyl.

21. The compound of claim 7, wherein R is N,N-di(lower)alkylcarbamoylnorbornyl.

22. The compound of claim 21, wherein R is 3-(N,N-diisopropylcarbamoyl)-2-norbornyl.

23. The compound of claim 7, wherein R is aminonorbornyl.

24. The compound of claim 23, wherein R is 3-amino-2-norbornyl.

25. The compound of claim 7, wherein R is 3-(lower)alkoxycarbonylamino-2-norbornyl.

26. The compound of claim 7, wherein R is carboxynorbornenyl.

27. The compound of claim 26, wherein R is 3-carboxy-5-norbornen-2-yl.

28. The compound of claim 7, wherein R is (lower)alkoxycarbonylnorbornenyl.

29. The compound of claim 28, wherein R is 3-methoxycarbonyl-5-norbornen-2-yl.

30. The compound of claim 28, wherein R is 3-ethoxycarbonyl-5-norbornen-2-yl.

31. The compound of claim 28, wherein R is 3-isopropoxycarbonyl-5-norbornen-2-yl.

32. The compound of claim 28, wherein R is 3-tert-butoxycarbonyl-5-norbornen-2-yl.

33. The compound of claim 7, wherein R is bicyclo[3,1,1]heptyl substituted by at least one lower alkyl group.

34. The compound of claim 33, wherein R is pinanyl.

35. The compound of claim 34, wherein R is 3-pinanyl.

36. The compound of claim 7, wherein R is (lower)alkoxycarbonylbicyclo[2,2,2]-octyl.

37. The compound of the claim 36, wherein R is 3-ethoxycarbonylbicyclo[2,2,2]oct-2-yl.

38. A pharmaceutical composition for the therapeutic treatment of cancer in mammals, comprising:
a therapeutically effective amount of the compound of claim 1 in association with a pharmaceutically acceptable, substantially nontoxic carrier or excipient.

39. A method for treating cancer which comprises administering a compound of the claim 1 to mammals.

* * * * *